(12) United States Patent
Jansen et al.

(10) Patent No.: US 10,160,861 B2
(45) Date of Patent: Dec. 25, 2018

(54) COUMARIN DYES AND CONJUGATES THEREOF

(71) Applicant: CYANAGEN S.r.l., Bologna (IT)

(72) Inventors: Thomas Paul Jansen, Granarolo dell'Emilia (IT); Giacomo Rodeghiero, Bologna (IT); Dario Foglietta, Cotignola (IT); Rossana Perciaccante, Granarolo dell'Emilia (IT); Leopoldo Della Ciana, Bologna (IT)

(73) Assignee: CYANAGEN S.r.l., Bologna (IT)

( * ) Notice: Subject to any disclaimer, the term of this patent is extended or adjusted under 35 U.S.C. 154(b) by 0 days.

(21) Appl. No.: 15/458,801

(22) Filed: Mar. 14, 2017

(65) Prior Publication Data
US 2017/0267866 A1    Sep. 21, 2017

(30) Foreign Application Priority Data
Mar. 15, 2016    (IT) .......................... 102016000027283

(51) Int. Cl.
| | | |
|---|---|---|
| *C07D 311/08* | (2006.01) | |
| *C07D 409/04* | (2006.01) | |
| *C09B 57/02* | (2006.01) | |
| *C07K 16/28* | (2006.01) | |
| *G01N 33/52* | (2006.01) | |
| *C07D 409/14* | (2006.01) | |
| *A61K 47/54* | (2017.01) | |

(52) U.S. Cl.
CPC ............ *C09B 57/02* (2013.01); *A61K 47/558* (2017.08); *C07D 409/04* (2013.01); *C07D 409/14* (2013.01); *C07K 16/2803* (2013.01); *C07K 16/2812* (2013.01); *G01N 33/52* (2013.01)

(58) Field of Classification Search
CPC .......................... C07D 311/08; C07D 409/04
USPC .................................................. 549/60, 399
See application file for complete search history.

(56) References Cited

U.S. PATENT DOCUMENTS

| | | |
|---|---|---|
| 5,696,157 A | 12/1997 | Wang et al. |
| 6,372,895 B1 | 4/2002 | Bentsen et al. |
| 8,431,416 B2 | 4/2013 | Diwu et al. |

FOREIGN PATENT DOCUMENTS

| | | | |
|---|---|---|---|
| EP | 1 535 969 A2 | | 6/2005 |
| EP | 2 236 508 A1 | | 10/2010 |
| EP | 3219712 | * | 9/2017 |
| WO | 2008076916 A2 | | 6/2008 |

OTHER PUBLICATIONS

Jordan, V. C. Nature Reviews: Drug Discovery, 2, 2003, 205.*
Dörwald, F. Zaragoza. Side Reactions in Organic Synthesis: A Guide to Successful Synthesis Design, Weinheim: Wiley-VCH Verlag GmbH & Co. KGaA, 2005, Preface.*
Jin, et. al., "Synthesis of 7-Aminocoumarin by Buchwald-Hartwig Cross Coupling for Specific Protein Labeling in Living Cells," ChemBioChem, 2011, 12: 65-70.
Kotchapradist, et al., "Synthesis, Characterisation, and Electroluminescence Properties of N-Coumarin Derivatives Containing Peripheral Triphenylamine," Eur. J. Org. Chem., 2015, 3:496-505.
Kotchapradist, et al., "N-Coumarin Derivatives as Hole-Transporting Emitters for High Efficiency Solution-Processed Pure Green Electroluminescent Devices," Dyes and Pigments, 2015, 112:227-235.
Schill, et al., "4-Trifluoromethyl-Substituted Coumarins with Large Stokes Shifts: Synthesis, Bioconjugates, and Their Use in Super-Resolution Fluorescence Microscopy," Chem. Eur. J., 2013, 19:16556-16565.
Italian Search Report and Written Opinion for App. No. 102016000027283, dated Jul. 13, 2016.
Bodanszky, M., "Active Esters," In: Principles of Peptide Synthesis, Springer-Verlag, pp. 28-36 (1984).
Dendrinos, K.G., et al., "Synthesis of N-Hydroxysuccinimide Esters Using Polymer Bound HOBT," Tetrahedron Letters, 39:1321-1324 (1998).
Hermanson, G.T., "The Reactions of Bioconjugation," In: Bioconjugate Techniques, Elsevier Science, pp. 229-258 (2013).

* cited by examiner

*Primary Examiner* — Douglas M Willis
(74) *Attorney, Agent, or Firm* — Vivicar Law, PLLC

(57) ABSTRACT

The present invention describes novel 7-alkylamino-3-(thienyl) coumarin fluorescent dyes of formula (I)

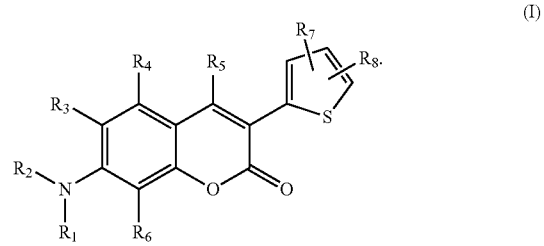

These dyes are water soluble, can be excited by the 405 nm excitation source and exhibit a large Stokes shift (≥80 nm). Furthermore, the dyes possess a reactive group for the labeling of biomolecules or other analytes.

17 Claims, 8 Drawing Sheets

COUMARIN DYES AND CONJUGATES THEREOF

FIELD OF THE INVENTION

The present disclosure concerns novel coumarin dyes and conjugates thereof.

BACKGROUND OF THE INVENTION

With the development of high power diode lasers and the commercialization of an economically viable excitation source in the visible range, the 405 nm diode laser has had a major impact in the biotechnology field, especially in flow cytometry, a laser-based, biophysical technology employed in cell counting, cell sorting, biomarker detection and protein engineering. The need for suitable dyes fitting the 405 nm excitation source has inspired researchers towards the development of short wavelength excitable dyes, showing large Stokes Shifts and suitable for bio-conjugation applications.

Coumarin dyes with large Stokes shifts (80 nm or higher) and high fluorescence quantum yield that are efficiently excited by a 405 nm laser source are rare.

Diwu et al in U.S. Pat. No. 8,431,416 describe halogenated 7-hydroxy coumarin dyes that can be used in flow cytometry applications.

Fluorescence of 7-hydroxy coumarins is pH dependent due to the intrinsically high pKa value of the C7-hydroxyl proton.

The protonated or neutral form of these dyes is not fluorescent. For these dyes to become fluorescent, complete deprotonation of the 7-hydroxyl proton is required to give the deprotonated or anionic form. At physiological pH these dyes exist in their neutral form and are not fluorescent and therefore not useful in biological assays.

The incorporation of chlorine atoms in the 6- and/or 8-position of the coumarin core structure lowers the $pK_a$ and allows these dyes to be useful near physiological pH. Nevertheless, a strong pH dependency is observed up to pH 6-6.5 and the chlorine atoms may impart a heavy atom effect with consequent reduction of fluorescent quantum yield as well as reduce water solubility. Furthermore, the anionic form of these dyes, required for fluorescence, may be undesirable in some applications as described by Jin et al in ChemBioChem, 2011, 12, 65-70.

On the contrary, 7-amino coumarins are known to be pK independent over a much wider pH range and show excellent photostability and high fluorescence quantum ylelds. The primary amine derivatives such as described by Haugland et al (U.S. Pat. No. 5,696,157) show absorption maxima near the UV (350 nm) and therefor are not suitable in flow cytometry applications with the 405 nm violet excitation source.

Tertiary, or N-di-alkylated, 7-amino coumarins are well known as for example, Alexa Fluor 430 among others. However, most of these dyes are not efficiently excited by a 405 nm laser source. Typical excitation maxima are observed in the 425-450 nm range with emission maxima between 460 and 490 nm.

Introduction of a 3-thienyl substituent into a 7-amino coumarin gives an absorption maximum near 400 nm and an emission maximum near 500 nm. Several other derivatives of 7-amino-3-thienyl coumarins have been described in literature as for example in EurJOC, 2015(3), 496-505 and Dyes and Pigments, 112, 227-235; 2015. These fluorophores have found widespread use in, for example, electroluminescence and dye sensitized solar cells.

However, none of these dyes is water soluble, they are extremely hydrophobic and do not possess a reactive group required for preparing fluorescent conjugates. It is well known that hydrophobic fluorophores tend to show high levels of quenching when conjugated to an analyte.

These quenching effects of the fluorophore may be the result of dye-dye self-quenching or are due to dye-analyte interactions. Self-quenching is caused mainly by hydrophobicity, proximity, high degrees of labeling and fluorophore size. Quenching due to dye-analyte interactions is also associated with the hydrophobicity of the fluorophore, where back folding of the fluorophore towards hydrophobic pockets of the anaiyte results in energy transfer processes between the dye and the hydrophobic side chains of amino acid residues in proteins (e.g. tryptophan and tyrosine).

Therefore, these dyes are not suitable as fluorescent markers in bio-conjugation applications.

BRIEF SUMMARY OF THE INVENTION

The object of the present invention is to provide novel coumarin dyes with strong absorption at 405 nm, high fluorescence, large Stokes shift, useful in bio-conjugation applications.

According to the invention, the above object is achieved thanks to the subject matter specified in the ensuing claims, which are understood as forming an integral part of the present description.

In an embodiment, the instant description discloses 7-amino-3-thienyl coumarin dyes of formula (I)

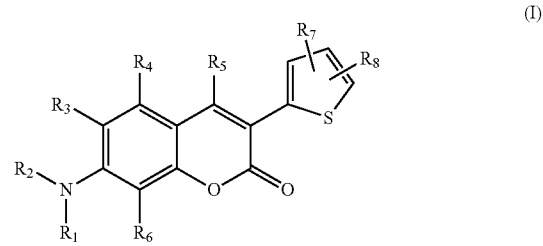

(I)

wherein

R1 is L-RG;

R2, R3, R4, R5, R6, R7 and R8 are independently selected from H, halogen, alkenyl, alkynyl, cyano, trifluoromethyl, aryloxy, azido, amino, hydroxyl, WSG, L-WSG, substituted or unsubstituted alkyl and substituted or unsubstituted alkoxy;

R2 together with R3 or R6 may form a substituted or unsubstituted 5- or 6-membered N-heterocycle;

RG is a chemically reactive group;

L is a linker;

WSG is a water soluble group;

with the proviso that at least one of R7 and R8 is WSG, and salts thereof.

In a further embodiment, the instant description discloses 7-amino-3-thienyl coumarin dye conjugates having the general formula (V):

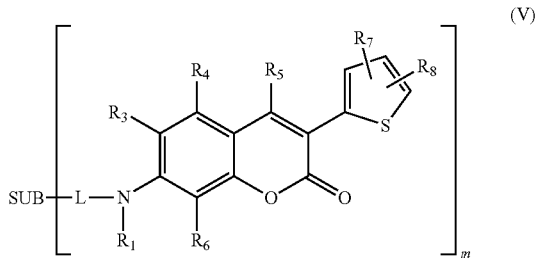

(V)

wherein

R2, R3, R4, R5, R6, R7 and R8 are independently selected from H, halogen, alkenyl, alkynyl, cyano, trifluoromethyl, aryloxy, azido, amino, hydroxyl, WSG, L-WSG, substituted or unsubstituted alkyl and substituted or unsubstituted alkoxy;

R2 together with R3 or R6 may form a substituted or unsubstituted 5- or 6-memfoered N-heterocycle;

L is a linker;

WSG is a water soluble group selected from sulfonic acid, sulfate, alkyl sulfonic acid, thiosulfonic acid, sulfonamide, phosphate, phosphonic acid, boronic acid, ammonium, pyridinium, quinolium, acridinium, cyclodextrin, monosaccharide, oligosaccharide, dextrane or polyetheleneglycol;

m is an integer number 1 to 25;

SUB is an amino acid, a peptide, a protein, a saccharide, a nucleoside, a nucleotide, an oligonucleotide, a nucleic acid, a hapten, a drug or a lipid;

with the proviso that and at least one of R7 and R8 is a sulfonic acid, and salts thereof.

The 7-amino-3-thienyl coumarin dyes of formula (I), as well as the relative conjugates of formula (V) show large Stokes shifts of at least 80 nm with efficient excitability by a 405 nm violet excitation source and high fluorescence intensities in the green, and are highly suitable for bioconjugation applications.

The instant description discloses the synthesis and properties of 7-amino-3-thienyl coumarin dyes of formula (I) that are useful for preparing fluorescent dye conjugates, in particular employed in, but not limited to, flow cytometry applications.

BRIEF DESCRIPTION OF THE SEVERAL VIEWS OF THE DRAWINGS

The invention will now be described in detail, purely by way of an illustrative and non-limiting example and, with reference to the accompanying drawings, wherein.

DETAILED DESCRIPTION OF THE INVENTION

Figure 1:
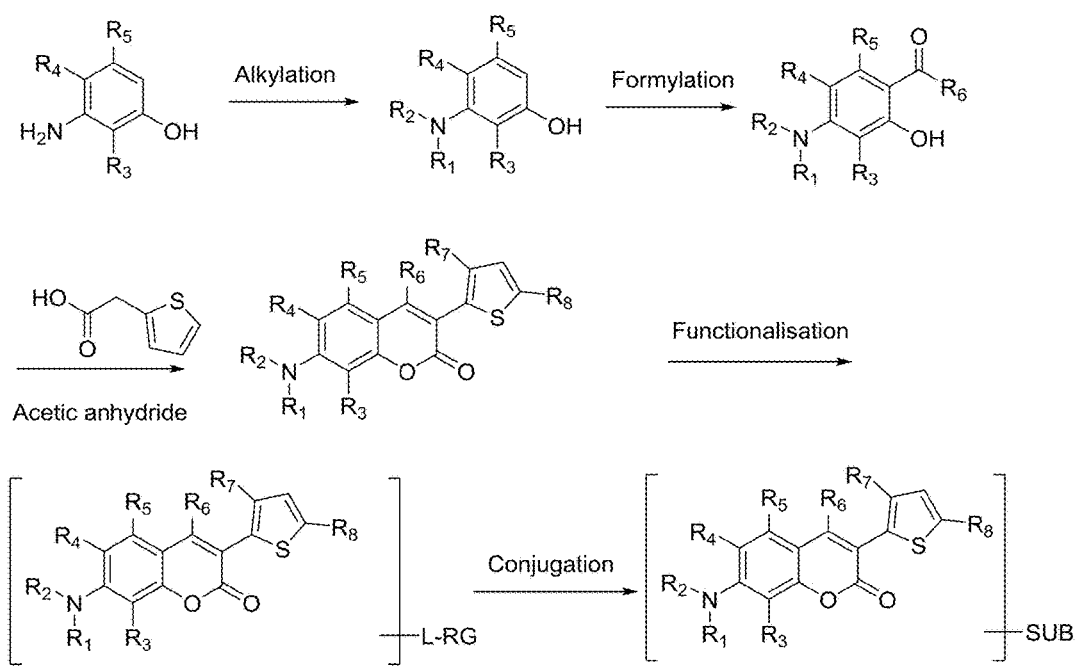
FIG. 1 shows the general reaction scheme for the synthesis of dyes disclosed in the instant description.

In the following description, numerous specific details are given to provide a thorough understanding of embodiments. The embodiments can be practiced without one or more of the specific details, or with other methods, components, materials, etc. In other instances, well-known structures, materials, or operations are not shown or described in detail to avoid obscuring aspects of the embodiments.

Reference throughout this specification to "one embodiment" or "an embodiment" means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The headings provided herein are for convenience only and do not interpret the scope or meaning of the embodiments.

In an embodiment, the instant description discloses 7-amino-3-thienyl coumarin dyes of formula (I):

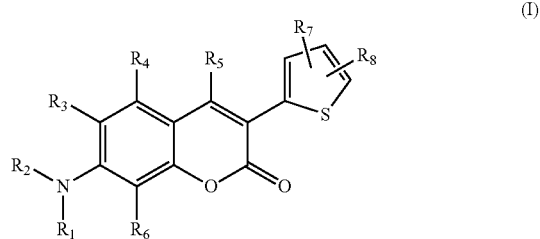

(I)

wherein

R1 is L-RG;

R2, R3, R4, R5, R6, R7 and R8 are independently selected from H, halogen, alkenyl, alkynyl, cyano, trifluoromethyl, aryloxy, azido, amino, hydroxyl, WSG, L-WSG, substituted or unsubstituted alkyl and substituted or unsubstituted alkoxy;

R2 together with R3 or R6 may form a substituted or unsubstituted 5- or 6-membered N-heterocycle;

RG is a chemically reactive group;

L is a linker;

WSG is a water soluble group;

with the proviso that at least one of R7 and R8 is WSG, preferably both R7 and R8 are WSG;

and salts thereof.

In an embodiment, RG is selected from: carboxylic acid, an activated ester of a carboxylic acid, carbodiimide, sulfonyl halide, acyl halide, silyl halide, acyl azide, acyl nitrile, acrylamide, amine, aldehyde, alkyl or aryl halide, alkyl sulfonate, sulfonate ester, anhydride, azide, aziridine, diazoalkane, haloacetamide, halotriazine, hydrazine, hydroxylamine, isocyanate, isothiocyanate, maieimide, phosphoramidate, thiol, hydroxyl, hydrazine and alkyne. Preferably RG is selected from carboxylic acid, an activated ester of a carboxylic acid, sulfonyl halide, acyl halide, amine, alkyl or aryl halide, anhydride, azide, haloacetamide, halotriazine, hydrazine, isocyanate, isothiocyanate, maieimide, phosphoramidate, thiol, hydroxyl and alkyne. More preferably RG is selected from carboxylic acid, an activated ester of a carboxylic acid, amine, azide, haloacetamide, hydrazine, isocyanate, maleimide and alkyne.

In an embodiment, L is a linker of formula (VI):

$[(CH_2)_a—Y—(CH_2)_b]_c$ (VI)

wherein Y can be the same or different for the various substltuents and is selected from none, O, S, NH, NR9, $SO_2$—NH, $SO_2$—NR9, CO—NH, CO—O, C=N—NHR9, CO—S, 1,3-triazole, CO—O—CO, aminotriazine, triazinyl ether, NH—CO—NH, NH—CS—NH, NH—CO—O, O—$POR_9$—O, O—Si, $SO_2$, $SO_2$—O, amino acid, aryl or heteroaryl, wherein R9 is alkyl or WSG, a and c can be the same or different and are an integer number 1 to 10, and b is an integer number 0 to 10.

In a preferred embodiment, Y can be the same or different for the various substituents and is selected from none, O, S, $SO_2$—NH, $SO_2$—NR9, CO—NH, CO—O, CO—S, 1,3-triazole, NH—CO—NH, NH—CS—NH, NH—CO—O, $SO_2$—O, aryl, heteroaryl and amino acid. More preferably, Y is selected from none, O, S, $SO_2$—NH, $SO_2$—NR9, CO—NH, CO—O and 1,3-triazole, wherein R9 has the meaning defined above.

In an embodiment, WSG is selected from sulfonic acid, sulfate, alkyl sulfonic acid, thiosulfonic acid, sulfonamide, phosphate, phosphonic acid, boronic acid, ammonium, pyridinium, quinolium, acridinium, cyclodextrin, monosaccharide, oligosaccharide, dextrane or —$(CH_2—CH_2—O)_x$ in which x is an integer number from 1 to 10. Preferably WSG is selected from sulfonic acid, alkyl sulfonic acid, sulfonamide, phosphate, phosphonic acid, ammonium, pyridinium, cyclodextrin, monosaccharide, oligosaccharide, dextrane and —$(CH_2—CH_2—O)_x$ in which x is an integer number from 1 to 10. More preferably WSG is selected from sulfonic acid, alkyl sulfonic acid, sulfonamide, ammonium and —$(CH_2—CH_2—O)_x$ in which x is an integer number from 1 to 10.

In an embodiment the salts of sulfonic acid, alkyl sulfonic acid, thiosulfonic acid, phosphonic acid and boronic acid are selected from alkaline metal ions and ammonium ion, preferably sodium, potassium, and an ammonium ion.

In a preferred embodiment, the 7-amino-3-thienyl coumarin dyes are represented by formula (II):

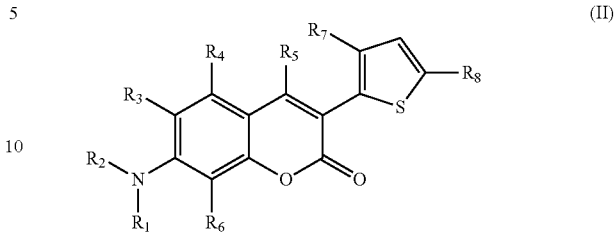

(II)

wherein

R1 is L-RG;

R2, R3, R4, R5, R6, R7 and R8 are independently selected from H, halogen, cyano, trifluoromethyl, hydroxyl, WSG, L-WSG, substituted or unsubstituted alkyl, and substituted or unsubstituted alkoxy;

R2 together with R3 or R6 may form a substituted or unsubstituted 5- or 6-membered N-heterocycle;

RG is a chemically reactive group as defined above;

L is a linker as defined above;

WSG is a water soluble group and is selected from sulfonic acid, sulfate, alkyl sulfonic acid, thiosulfonic acid, sulfonamide, phosphate, phosphonic acid, boronic acid, ammonium, pyridinium, quinolium, acridinium, cyclodextrin, monosaccharide, oligosaccharide, dextrane and polyetheleneglycol;

with the proviso that at least one of R7 and R8 is sulfonic acid, preferably both R7 and R8 are sulfonic acid;

and salts thereof.

In a still further preferred embodiment, the 7-amino-3-thienyl coumarin dyes are represented by formula (III):

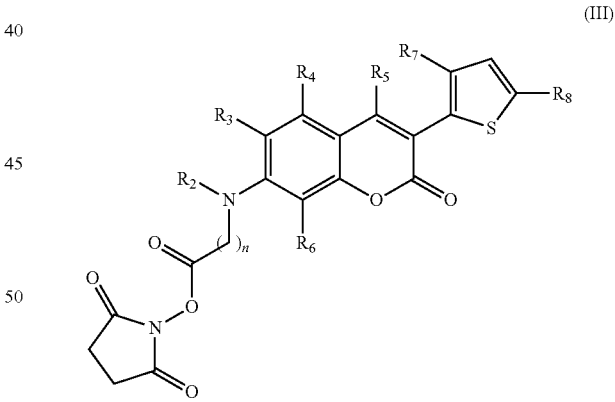

(III)

wherein

R2 is selected from substituted or unsubstituted alkyl, L-WSG;

R3, R4, R5, R6, R7 and R8 are independently selected from H, halogen, hydroxyl, cyano, substituted or unsubstituted alkyl, and substituted or unsubstituted alkoxy;

R2 together with R3 or R6 may form a substituted or unsubstituted 5- or 6-membered N-heterocycle;

L is a linker as defined above;

WSG is a water soluble group as defined above;

n is an integer number 1 to 10;

at least one of R7 and R8 is sulfonic acid, preferably both R7 and R8 are sulfonic acid;

and salts thereof.

In a still further preferred embodiment, the 7-amino-3-thienyl coumarin dyes are represented by formula (IV):

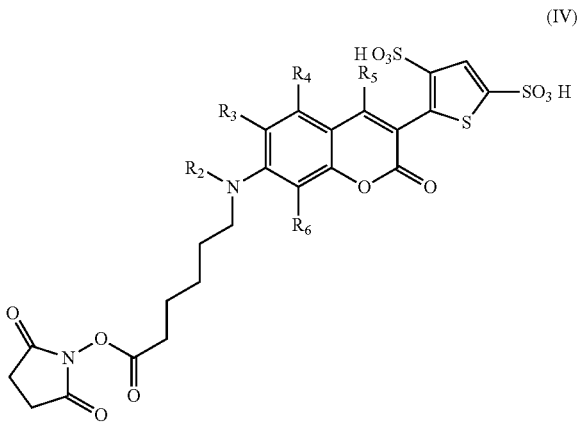

wherein

R2 is selected from substituted or unsubstituted alkyl, L-WSG;

R3, R4, R5, R6 are H;

R2 together with R3 or R6 may form a substituted or unsubstituted 5- or 6-membered N-heterocycle;

L is a linker as defined above;

WSG is a water soluble group as defined above;

and salts thereof.

The 7-amino-3-thienyl coumarin dyes of formulas (I) to (IV) show large Stokes shifts of at least 80 nm with efficient excitability by a 405 nm violet excitation source and high fluorescence intensities in the green, and are highly suitable for bio-conjugation applications.

In a further embodiment, the instant description discloses 7-amino-3-thienyl coumarin dye conjugates having the general formula (V):

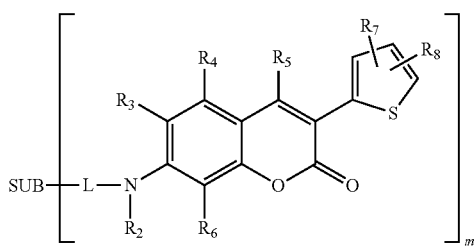

wherein

R2, R3, R4, R5, R6, R7 and R8 are independently selected from H, halogen, alkenyl, alkynyl, cyano, trifluoromethyl, aryloxy, azido, amino, hydroxyl, WSG, L-WSG, substituted or unsubstituted alkyl and substituted or unsubstituted alkoxy;

R2 together with R3 or R6 may form a substituted or unsubstituted 5- or 6-membered N-heterocycle;

L is a linker as defined above;

WSG is a water soluble group and is selected from sulfonic acid, sulfate, alkyl sulfonic acid, thiosulfonic acid, sulfonamide, phosphate, phosphonic acid, boronic acid, ammonium, pyridinium, quinolium, acridinium, cyclodextrin, monosaccharide, oligosaccharide, dextrane or —(CH$_2$—CH$_2$—O)$_x$ in which x is an integer number from 1 to 10;

m is an integer number 1 to 25;

SUB is an amino acid, a peptide, a protein, a saccharide, a nucleoside, a nucleotide, an oligonucleotide, a nucleic acid, a hapten, a drug or a lipid;

with the proviso that at least one of R7 and R8 is a sulfonic acid, preferably both R7 and R8 are sulfonic acid, and salts thereof.

In a preferred embodiment, residues R7 and R8 of formula (V) are bound to the thienyl ring in positions 2 and 4, and are sulfonic acid groups or salts thereof.

In a preferred embodiment, residues R3, R4, R5 and R6 of formula (V) are hydrogen atoms.

In a preferred embodiment, residues R2 of formula (V) is substituted or unsubstituted alkyl or L-WSG.

In order that the invention herein described may be fully understood, a number of terms are explicitly defined, below.

The term "7-amino-3-thienyl coumarin", as used herein, means any dye compound containing as core structure the following one:

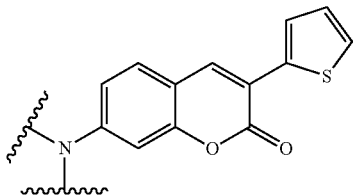 [SMILES: *N(*)c1ccc2cc(-c3cccs3)c(=O)oc2c1]

It is to be understood that the dye compounds as disclosed in the instant description can be formally drawn with other permitted resonance structures.

The term 'tertiary' or 'N-di-alkylated 7-amino coumarin' means a dye compound in which the 7-amino group of the coumarin dye is substituted two times by a carbon atom that is itself optionally substituted.

The term "substituted" refers to the formal replacement of a hydrogen atom on a chemical moiety or functional group with an alternative radical. The alternative radical substituent moiety is selected from hydroxy, trifluoromethyl, halogen, alkoxy, aminoalkyl, aminoalkoxy, amino, monoalkylamino, dialkylamino, alkylcarbonylamino, alkoxycarbonylamino, alkoxycarbonyl, carboxy, hydroxyalkoxy, alkoxyalkoxy, monoalkylaminoalkoxy, (carboxyalkyl)amino, alkoxycarbonyl, alkynylcarbonyl, alkylsulfonyl, alkenylsulfonyl, alkynylsulfonyl, arylsulfonyl, alkylsulfonamido, arylsulfonamido, carboxyalkoxy, carboxyalkyl, carboxyalkylamino, cyano, trifluoromethoxy, guanidine, alkyl azide, azide, alkylthio (disulfide), acrylo, aryl, arylalkyl, heteroaryl, heteroarylalkyl, cycloalkylalkyl, cycloalkenylalkyl, cycloheteroalkylalkyl, cycloheteroalkenylalkyl or WSG. Preferably, the alternative radical substituent moiety is selected from hydroxy, trifluoromethyl, halogen, alkoxy, dialkylamino, alkylcarbonylamino, alkoxycarbonylamino, alkoxycarbonyl, hydroxyalkoxy, alkoxyalkoxy, alkylsulfonamido, arylsulfonamido, carboxyalkoxy, carboxyalkylamino, cyano, alkyl azide, azide, aryl, arylalkyl, heteroaryl, heteroarylalkyl, cycloalkylalkyl, cycloalkenylalkyl, cycloheteroalkylalkyl, cycloheteroalkenylalkyl or WSG. More preferably, the alternative radical substituent moiety is selected from hydroxy, trifluoromethyl, halogen, alkoxy, dialkylamino, alkylcarbonylamino, alkoxyalkoxy, alkylsulfonamido, arylsulfonamido, cyano, azide, aryl, heteroaryl or WSG. Still more preferably, the alternative radical substituent moiety is selected from hydroxy, trifluoromethyl, halogen, alkoxy, dialkylamino, alkylcarbonylamino, alkoxyalkoxy, alkylsulfonamido, arylsulfonamido, cyano, aside, aryl, or heteroaryl.

As used herein, "alkyl" is intended to include both branched, linear and cyclic saturated aliphatic hydrocarbon groups. Preferably, "alkyl" means branched, straight-chain or cyclic alkyl group having from 1 to 10 carbon atoms, more preferably 1 to 6 carbon atoms.

As used herein, "alkoxy" represents an alkyl group singular bonded to an oxygen atom. Preferably, "alkoxy" means branched, straight-chain or cyclic alkoxy group having from 1 to 10 carbon atoms, more preferably 1 to 6 carbon atoms.

The term "alkenyl" refers to a non-aromatic, linear, branched or cyclic hydrocarbon group containing at least one carbon to carbon double bond. Preferably, "alkenyl" means non-aromatic, linear, branched or cyclic alkenyl group having from 2 to 10 carbon atoms, more preferably 2 to 6 carbon atoms.

The term "alkynyl" refers to a linear, branched or cyclic hydrocarbon group, containing at least one carbon to carbon triple bond. Preferably, "alkynyl" means linear, branched or cyclic alkynyl group having from 2 to 10 carbon atoms, more preferably 2 to 6 carbon atoms.

The term "carboxylic acid" is intended to mean an organic compound that contains a carteoxyl group (C(=O)OH).

The term "aryl" is intended to mean any stable monocyclic or polycyclic carbon ring of up to 7 atoms in each ring wherein at least one ring is aromatic.

The term "heteroaryl" is intended to mean any stable monocyclic or polycyclic carbon ring of up to 7 atoms in each ring wherein at least one ring is aromatic and at least one ring contains a heteroatom in which the heteroatom is selected from N, O or S, preferably N.

The term "N-heterocycle" means a saturated or unsaturated 5 or 6-membered ring that contains at least one N atom.

The term "reactive group", or "RG" as used herein, means a functional group present on the dye compound that is capable of chemically reacting with a functional group on a different compound to form a covalent linkage.

The term "linker" or "L" as used herein, means a chemical moiety that connects the core structure of the dye compound disclosed in the instant description to RG or WSG or SUB.

The term "water-soluble group" or "WSG", as used herein, means any substituent that enhances the water-solubility of a dye compound of the present description.

The term "dye-conjugate" refers to a conjugate between a dye compound of the present invention and a substrate "SUB".

The term "substrate" or "SUB" as used herein means any organic or inorganic "detection reagent" useful for detecting an anaiyte of interest present in a sample to be analyzed.

The term "analyte" as used herein means any substance to be analyzed, detected, measured, or labeled. Examples of analytes which can be detected by means of the dyes or dye-conjugates disclosed herein include, but are not limited to, proteins, peptides, hormones, haptens, antigens, antibodies, receptors, enzymes, nucleic acids, polysaccharides, chemicals, polymers, pathogens, toxins, organic drugs, inorganic drugs, cells, tissues, microorganisms, viruses, bacteria, fungi, algae, parasites, allergens, pollutants, and combinations thereof.

"Detection reagents" are represented by any "analyte-specific reagents" that bind preferably to the anaiyte of interest and are generally selected from members of a binding pair. Either member of the pair can be used as the analyte-specific reagent in order to selectively bind to the other member of the pair, wherein in some cases one of the members of the pair is the anaiyte to be detected. Examples of analyte-specific reagent pairs include, but are not limited to, biotin/avidin, streptavidin, anti-biotin antibody; IgG/protein; drug/drug receptor; Toxin/Toxin receptor; Peptide/Peptide receptor; Nucleotide/Complimentary nucleotide; Protein/Protein receptor; Enzyme substrate/Enzyme; Nucleic acid/Nucleic acid; Hormone/Hormone receptor; Target molecule/RNA or DNA aptamer.

The dye compounds disclosed herein can react through the RG residue with a wide variety of substrates "SUB" that contain or are modified to contain functional groups with suitable reactivity, resulting in chemical attachment of the dye compound to the substrate SUB. Typically, the conjugation reaction between the dye and the functional groups on the substrate results in one or more atoms of the reactive group RG to be incorporated into a new linkage attaching the dye to the substrate.

Examples of reactive groups present either on the dye or on SUB, along with the covalent linkage resulting from their reaction, are shown in Table 1.

TABLE 1

| Reactive pairs | | Resulting Linkage |
| --- | --- | --- |
| activated esters | amines/anilines | carboxamides |
| acrylamides | thiols | thioethers |
| acyl azides* | amines/anilines | carboxamides |
| acyl halides | amines/anilines | carboxamides |
| acyl halides | alcohols/phenols | esters |
| acyl nitriles | alcohols/phenols | esters |
| acyl nitriles | amines/anilines | carboxamides |
| aldehydes | amines/anilines | imines |
| aldehydes or ketones | hydrazines | hydrazones |
| alkyl halides | amines/anilines | alkyl amines |
| alkyl halides | carboxylic acids | esters |
| alkyl halides | thiols | thioethers |
| alkyl halides | alcohols/phenols | ethers |
| alkyl sulfonates | carboxylic acids | esters |
| alkyl sulfonates | alcohols/phenols | ethers |
| alkyl sulfonates | thiols | thioethers |
| anhydrides | alcohols/phenols | esters |
| anhydrides | amines/anilines | carboxamides |
| azide | alkyne | 1,3 triazole |
| aziridines | thiols | thioethers |
| carbodiimides | carboxylic acids | N-acylureas or anhydrides |
| diazoalkanes | carboxylic acids | esters |
| haloacetamides | thiols | thioethers |
| halotriazines | amines/anilines | aminotriazines |
| halotriazines | alcohols/phenols | triazinyl others |
| isocyanates | amines/anilines | areas |
| isocyanates | alcohols/phenols | urethanes |
| isothiocyanates | amines/anilines | thioureas |
| maleimides | thiols | thioethers |
| phosphoramidites | alcohols | phosphite esters |
| silyl halides | alcohols | silyl ethers |
| sulfonate esters | amines/anilines | alkyl amines |
| sulfonate esters | thiols | thioethers |
| sulfonate esters | carboxylic acids | esters |
| sulfonate esters | alcohols | ethers |
| sulfonyl halides | amines/anilines | sulfonamides |
| sulfonyl halides | phenols/alcohols | sulfonate esters |

*Acyl azides can also rearrange to isocyanates.

Within the present description, with the expression "activated ester of a carboxylic acid" is meant the ester of a carboxylic acid containing a good leaving group. Activated esters, as understood in the art, generally have the formula —COW (or —(CO)W), where W is a good leaving group, wherein the leaving group W is selected from succirainidyloxy (—OC$_4$H$_4$O$_2$) sulfosuccinimidyloxy (—OC$_4$H$_3$O$_2$—SO$_3$H), -1-oxybenzotriazolyl (—OC$_2$H$_4$N$_3$), an aryloxy or aryloxy group substituted one or more times by electron withdrawing substituents such as nitro, fluoro, chloro, cyano, or trifluoromethyl, or combinations thereof, used to form activated aryl esters, or a carboxylic acid activated by a carbodiimide to form an anhydride or mixed anhydride —OCOAlk or —OCN(Alk1)NH(Alk2), wherein Alk1 and Alk2, which may be the same or different, are selected from C$_1$-C$_{20}$ alkyl, C$_1$-C$_{20}$ perfluoroalkyl, C$_1$-C$_{20}$ alkoxy, cyclohexyl, 3-dimethylaminopropyl, and N-morpholinoethyl.

Where RG is an activated ester of a carboxylic acid, the dye of formula (I) is particularly useful for preparing dye-conjugates of proteins, nucleotides, oligonucleotides, or haptens.

Where RG is a maieimide or haloacetamide the reactive dye is particularly useful for conjugation to thiol-containing substrate.

Where RG is a hydrazide, the dye of formula (I) is particularly useful for conjugation to periodate-oxidized carbohydrates and glycoproteins, and, in addition, is an aldehyde-fixable polar tracer for cell microinjection.

Where RG is an azide, the dye of formula (I) is particularly useful for conjugation to alkyne-containing substrates by means of a Cu(I) catalyzed 1,3-dipolar cycloaddition reaction.

In a further embodiment, the present description concerns kits that facilitate the practice of various assays using any of the dyes herein disclosed. The kits typically comprise a fluorescent dye of formula (I) or a dye-conjugate of formula (V) in dry or solution form together with at least one more component. The other component of the kit is selected from a buffering agent such as labelling buffer, running buffer and washing buffer, an additional detection reagent such as a fluorescent dye or dve-conjugate different from the dye or dye-conjugate described herein that can be useful in multi-anaivte assays, a purification column that can be useful for purifylng the resulting labeled substance and an organic solvent to dissolve the fluorescent dye if present, in dry form.

The 7-amino-3-thienyl coumarin dyes of formula (I) are characterized by an absorption maximum at 410 nm±10 nm with a large Stokes Shift of at least 80 nm and an emission maximum at 510 nm±10 nm in the green.

Figure 3:
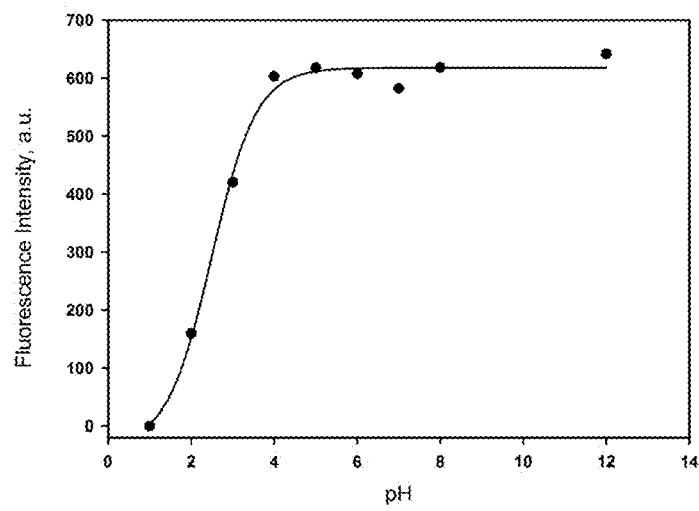
FIG. 3 shows a curve of the pH dependency on fluorescence of compound 6.

7-amino-3-thienyl coumarin dyes of the present invention are pH independent over a wide pH range as shown e.g. in FIG. 3 for compound 6. This aspect offers one advantage over 7-hydroxy coumarins that are pH dependent, due to high pKa values of the hydroxyl group and are poorly fluorescent at physiologic pH.

7-amino-3-thienyl coumarin dyes, that are themselves substituted twice by WSG on the thienyl ring, provides a dye with an absorption maximum near 405 nm and an emission maximum near 500 nm.

The absorption maximum at 410±10 nm provides a dye that is useful for applications in which a dye-conjugate can be detected with high sensitivity after excitation with a 405 nm violet excitation source.

Figure 9A:
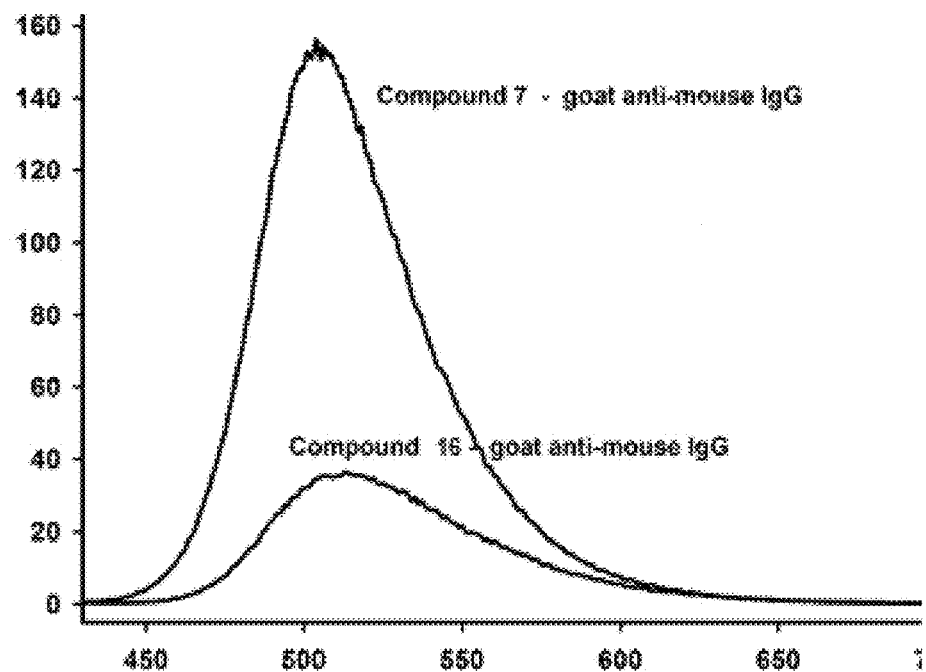
FIGS. 9a and 9b show full emission spectra (FIG. 9a) and integrated fluorescence intensity histogram (FIG. 9b) for a goat anti-mouse antibody labeled with either Compound 7 and compound 16 at equal antibody concentration and dye-to-protein ratio when excited at 420 nm.
Figure 9B:
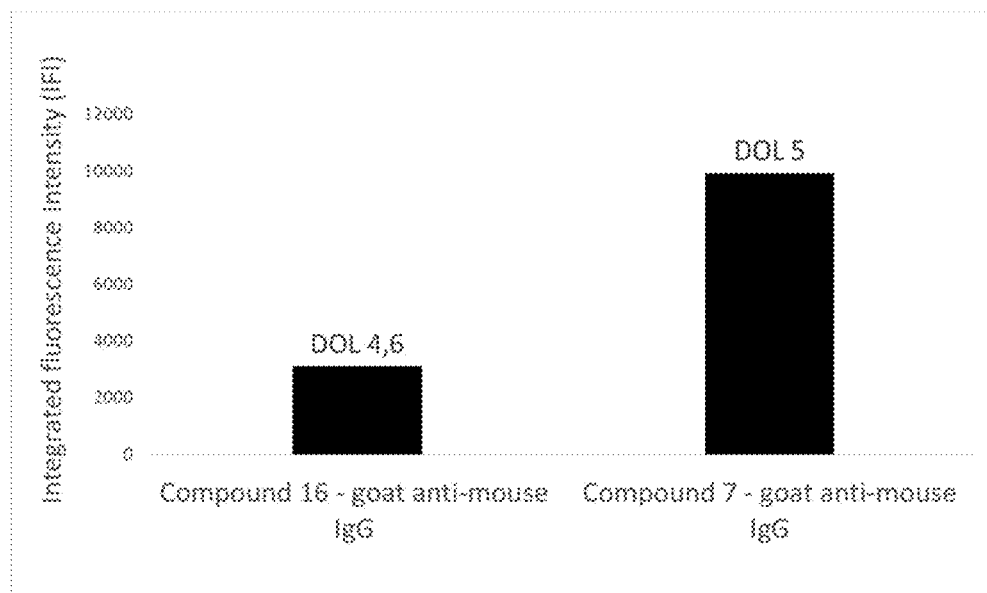

The introduction of at least one water soluble group onto the thienyl moiety increases the hydrophilicity of the dye, while retaining the optimal spectroscopic properties. Furthermore, the positioning of the water soluble group(s) onto the thienyl ring substantially lower quenching effects due to dye-dye or dye-substrate interactions upon conjugation, resulting in a higher total fluorescence of the dye conjugate in comparison to the corresponding 7-amino-3-thienyl coumarin dye, that is not substituted on the thienyl ring, as shown in FIGS. 9a and 9b. Particularly preferred water soluble group(s) present on the thienyl moiety is sulfonic acid and salts thereof. Sulfonic acid or salts thereof provide, in fact, a fluorescent dye with optimal water solubility, low molecular weight, excellent conjugation performance and highly fluorescent conjugates.

The large Stokes shift provides a dye, after conjugation with a substrate, which is extremely useful for multiplex applications in biological assays, which utilize the 405 nm violet excitation source. The spectral separation of various fluorophores into distinct excitation or acquisition channels is essential for multiplex anaiyte detection.

Preferred 7-amino-3-thienyl coumarin dyes of formula (I) are shown in Table 2.

TABLE 2

| Dye | Structure |
|---|---|
| sodium 5-(7-((5-carboxypentyl)(ethyl)amino)-2-oxo-2H-chromen-3-yl)thiophene-2,4-disulfonate (compound 6) | 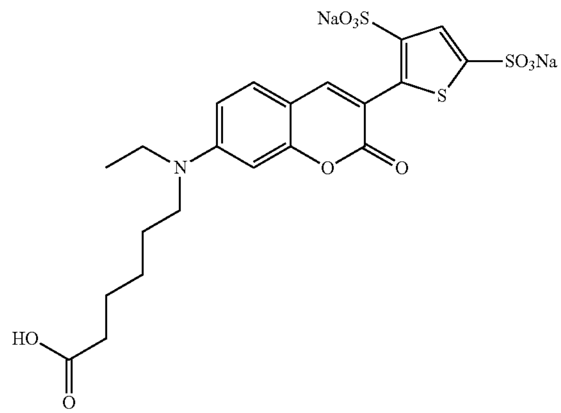 |

TABLE 2-continued

| Dye | Structure |
|---|---|
| Sodium 5-(7-((6-((2,5-dioxopyrrolidin-1-yl)oxy)-6-oxohexyl)(ethyl)amino)-2-oxo-2H-chromen-3-yl)thiophene-2,4-disulfonate (compound 7) | 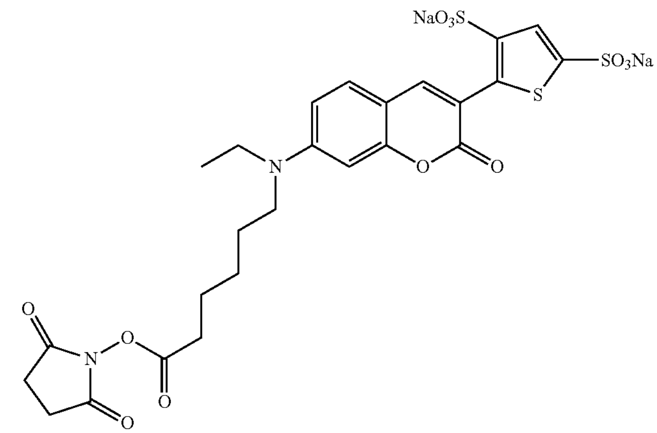 |
| sodium 5-(7-(ethyl(6-hydrazinyl-6-oxohexyl)amino)-2-oxo-2H-chromen-3-yl)thiophene-2,4-disulfonate (compound 8) | 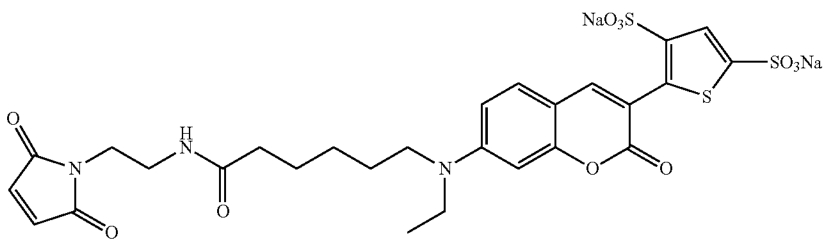 |
| sodium 5-(7-((6-((2-(2,5-dioxo-2,5-dihydro-1H-pyrrol-1-yl)ethyl)amino)-6-oxohexyl)(ethyl)amino)-2-oxo-2H-chromen-3-yl)thiophene-2,4-disulfonate (compound 9) | 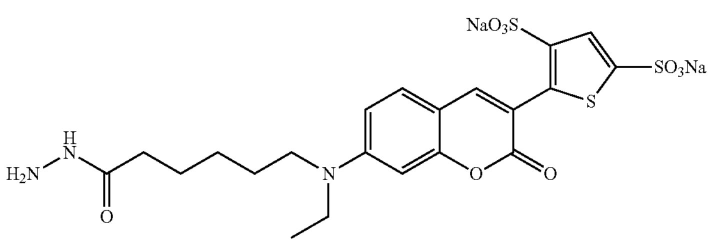 |
| Sodium 5-(7-((6-((2,5-dioxopyrrolidin-1-yl)oxy)-6-oxohexyl)(3-sulfonatopropyl)amino)-2-oxo-2H-chromen-3-yl)thiophene-2,4-disulfonate (compound 15) | 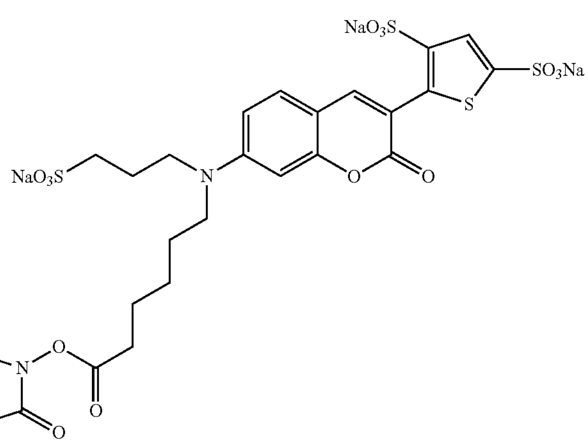 |

TABLE 2-continued

| Dye | Structure |
| --- | --- |
| sodium 5-(9-(6-((2,5-dioxopyrrolidin-1-yl)oxy)-6-oxohexyl)-2-oxo-6,7,8,9-tetrahydro-2H-pyrano[3,2-g]quinolin-3-yl)thiophene-2,4-disulfonate (compound 22) | 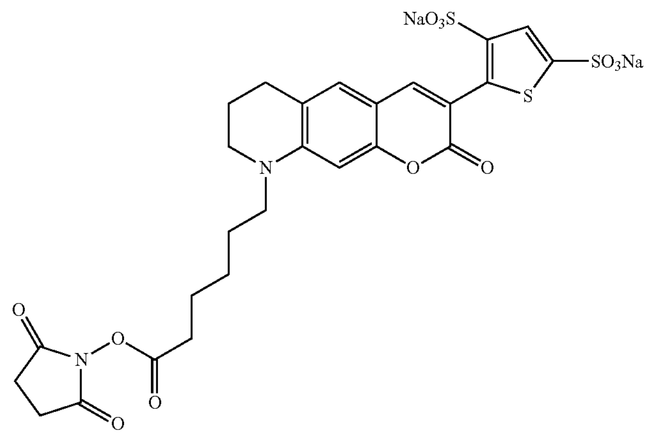 |
| 5-(7-((6-((2,5-dioxopyrrolidin-1-yl)oxy)-6-oxohexyl)(2-(2-methoxyethoxy)ethyl)amino)-2-oxo-2H-chromen-3-yl)thiophene-2,4-disulfonic acid | |
| 5-(7-((6-((2,5-dioxopyrrolidin-1-yl)oxy)-6-oxohexyl)(2-(2-methoxyethoxy)ethyl)amino)-2-oxo-2H-chromen-3-yl)thiophene-2,4-disulfonic acid | |

TABLE 2-continued

| Dye | Structure |
| --- | --- |
| 5-(7-((6-((2,5-dioxopyrrolidin-1-yl)oxy)-6-oxohexyl)(3-(N-(2-sulfoethyl)sulfamoyl)propyl)amino)-2-oxo-2H-chromen-3-yl)thiophene-2,4-disulfonic acid | 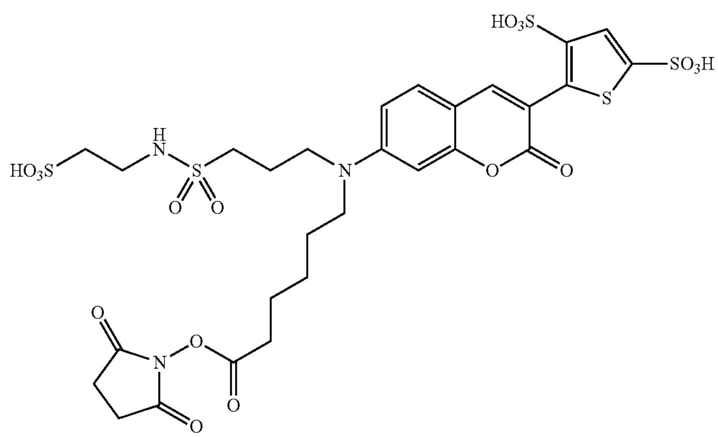 [SMILES: O=C(CCCCCN(CCCS(=O)(=O)NCCS(=O)(=O)O)c1ccc2cc(-c3sc(S(=O)(=O)O)cc3S(=O)(=O)O)c(=O)oc2c1)ON1C(=O)CCC1=O] |
| 5-(7-((3-(N-(6-((2,5-dioxopyrrolidin-1-yl)oxy)-6-oxohexyl)sulfamoyl)propyl)(ethyl)amino-2-oxo-2H-chromen-3-yl)thiophene-2,4-disulfonic acid | 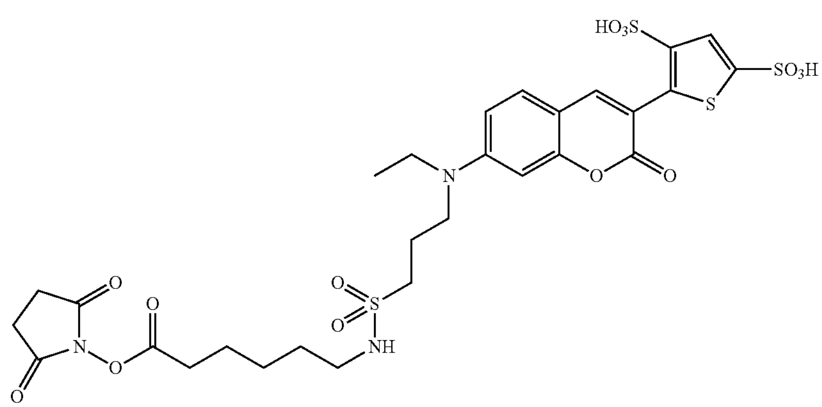 [SMILES: CCN(CCCS(=O)(=O)NCCCCCC(=O)ON1C(=O)CCC1=O)c1ccc2cc(-c3sc(S(=O)(=O)O)cc3S(=O)(=O)O)c(=O)oc2c1] |
| 5-(7-((4-(((2,5-dioxopyrrolidin-1-yl)oxy)carbonyl)benzyl)(ethyl)amino)-2-oxo-2H-chromen-3-yl)thiophene-2,4-disulfonic acid | 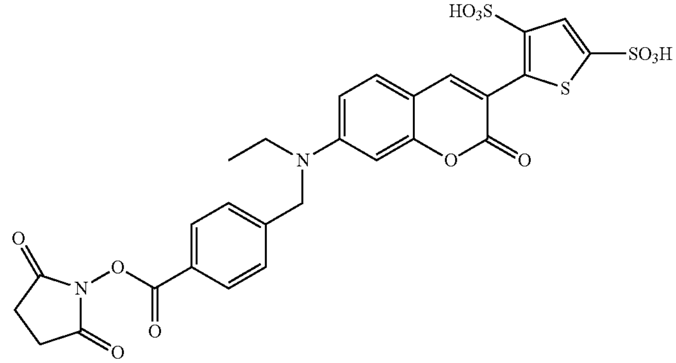 [SMILES: CCN(Cc1ccc(C(=O)ON2C(=O)CCC2=O)cc1)c1ccc2cc(-c3sc(S(=O)(=O)O)cc3S(=O)(=O)O)c(=O)oc2c1] |

TABLE 2-continued

| Dye | Structure |
|---|---|
| 2,5-dioxopyrrolidin-1-yl 6-((3-(3,5-disulfamoylthiophen-2-yl)-2-oxo-2H-chromen-7-yl)(ethyl)amino) hexanaote | 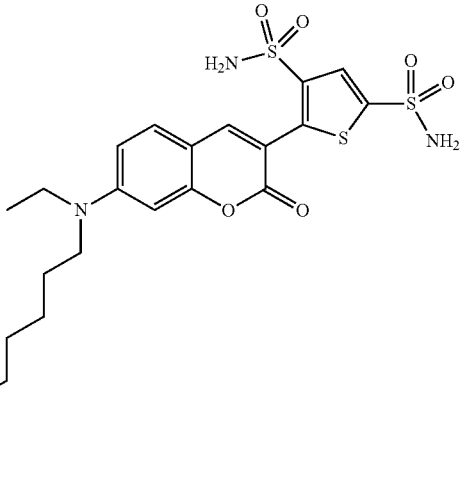 |

The number of the dyes in table 2 corresponds to the numbering of the compounds described in the examples.

EXAMPLES

In the following examples, the synthesis of selected dyes, the synthesis of selected conjugates, their characterization, and methods of use are provided. Further modifications and permutations will be obvious to those skilled in the art. The examples illustrate the practice of the invention and are not intended to limit or define the entire scope of the invention.

The dye compounds disclosed herein are synthetized in accord to the general synthesis scheme shown in FIG. 1. The synthesis of dye compounds of the present description is achieved by amine-alkylation of 3-amino phenols followed by a Vilsmeijer formylation to provide the intermediate salicylaidehyde derivative. Next, an acetic anhydride mediated condensation with thiophene acetic acid gives the dye core structure. Final functionalization provides the chemically reactive dye required for bioconjugation to provide fluorescent dye conjugates according to the instant description.

Those skilled in the art will appreciate that other synthetic routes may be used to synthesize the dyes of the invention. Although specific starting materials and reagents are discussed below, other starting materials and reagents can be easily substituted to provide a variety of derivatives and/or reaction conditions. In addition, many of the dyes prepared by the methods described below can be further modified in light of this disclosure using conventional chemistry well known to those skilled in the art. A more detailed description of the individual reaction steps is shown in the examples.

Example 1

Ethyl 6-((3-hydroxyphenyl)aminohexanoate, Compound 1

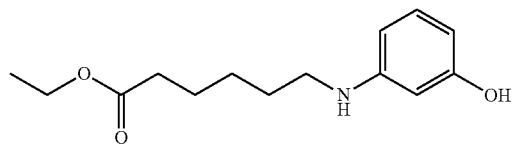 [SMILES: CCOC(=O)CCCCCNc1cccc(O)c1]

In a 100 mL round bottom, one necked flask set up with a magnetic stir bar and a reflux condenser, 3-aminophenol (40.0 g, 367 mmol) was dissolved in DMF. Ethyl-6-bromo hexanoate (16.4 g, 73 mmol) was added. The reaction mixture was stirred at 50° C. for 20 h. Solvent was removed under vacuum to give a crude oil. The crude oil was purified on a silica gel column with a gradient of hexanes/ethylacetate as eluent to yield the desired product, compound 1, as a colorless oil. The yield was 13.7 g (74%, based on ethyl-6-bromo hexanoate).

Analysis: 1H NMR (CDCl3, 600 MHz) δ7.00 (t, 1H, J=8.2 Hz), 6.17 (m, 2H), 6.09 (t, 1H, J=2.3 Hz), 4.13 (q, 2H, J=7.4 Hz), 3.08 (t, 2H, J=7.0 Hz), 2.30 (t, 2H, J=7.4 Hz), 1.71-1.58 (m, 4H), 1.46-1.38 (m, 2H), 1.26 (t, 3H, J=7.0 Hz).

Example 2

Ethyl 6-(ethyl(3-hydroxyphenyl)amino)hexanoate, Compound 2

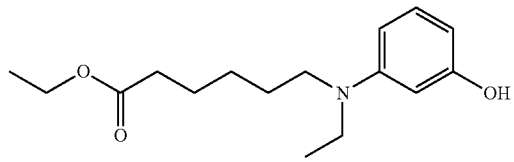 [SMILES: CCOC(=O)CCCCCN(CC)c1cccc(O)c1]

In a 100 mL round bottom, one necked flask set up with a magnetic stir bar and a reflux condenser, compound 1 (5.3 g, 21.1 mmol) was dissolved in DMF. Ethyl iodide (3.29 g, 21.1 mmol) and potassium carbonate (2.92 g, 21.1 mmol) were added. The reaction mixture was stirred at 50° C. for 20 h. Solvent was removed under vacuum to give a crude oil. The crude oil was dissolved in ethyl acetate (250 mL) and extracted with aqueous HCl (0.05M, 2×200 ml). The organic phase was dried over sodium sulfate and solvent was removed under vacuum to give a crude oil. The crude oil was purified on a silica gel column with a gradient of hexanes/ethylacetate as eluent to yield the desired product, compound 2 as a colorless oil. The yield was 5.1 g (86%).

Analysis: 1H NMR (CDCl3, 600 MHz) δ7.04 (t, 1H, J=8.2 Hz), 6.23 (d, 1H, J=8.2 Hz), 6.16 (s, 1H), 6.12 (d, 1H, J=7.6 Hz), 5.13 (broad band, 1H), 4.14 (q, 2H, J=7.0 Hz), 3.31 (q, 2H, J=7.0 Hz), 3.21 (t, 2H, J=7.6 Hz), 2.32 (t, 2H, J=7.0 Hz), 1.70-1.66 (m, 2H), 1.62-1.57 (m, 2H), 1.38-1.33 (m, 2H), 1.26 (t, 3H, J=7.0 Hz), 1.13 (t, 3H, J=7.0 Hz).

Example 3

Ethyl 6-(ethyl(4-formyl-3-hydroxyphenyl)aminohexanoate, Compound 3

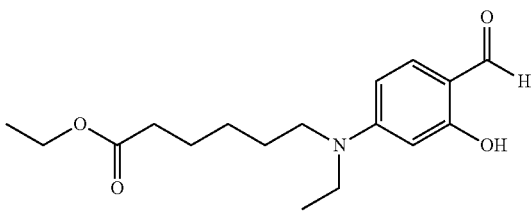 [SMILES: CCOC(=O)CCCCCN(CC)c1ccc(C=O)c(O)c1]

A flame dried two necked 100 mL round bottom flask equipped with stir bar was cooled to 0° C. Anhydrous DMF (14.5 mL, 188 mmol) was added, followed by slow addition of POCl₃ (8.7 mL, 94 mmol). The reaction mixture was then stirred at 0° C. for 30 min. and an additional 30 min. at room temperature. A solution of Compound 2 (3.5 g, 12.5 mmol) in DMF (anh, 10 mL) was slowly added at room temperature (RT) and the reaction mixture was stirred at RT for 20 h. The reaction mixture was cooled to 0° C. and quenched by addition of small pieces of ice at a time. The pH was neutralized to pH 8-10 with 1M NaOH. The aqueous solution was extracted with DCM (2×250 mL). Solvent was removed under vacuum to give a crude oil. The crude oil was purified on a silica gel column with a gradient of hexanes/ethylacetate as eluent to yield the desired product, compound 3 as a colorless oil. The yield was 2.0 g (53%)

Analysis: HNMR (CDCl3, 600 MHz) purity>98%. δ11.62 (s, 1H), 9.18 (s, 1H), 7.25 (d, 1H, J=8.8), 6.23 (dd, 1H, J=8.8, 2.3), 6.04 (d, 1H, J=2.3), 4.13 (q, 2H, J=7.0), 3.40 (q, 2H, J=7.0), 3.30 (t, 2H, J=7.6), 2.31 (t, 2H, J=7.6), 1.70-1.60 (m, 4H), 1.37 (m, 2H), 1.25 (t, 3H, J=7.6), 1.19 (t, 3H, J=7.0).

Example 4

Ethyl 6-(ethyl(2-oxo-3-(thiophen-2-yl)-2H-chromen-7-yl)aminohexanoate, Compound 4

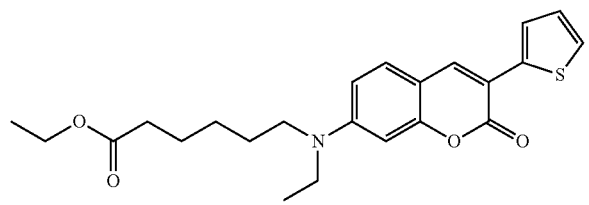 [SMILES: CCOC(=O)CCCCCN(CC)c1ccc2cc(-c3cccs3)c(=O)oc2c1]

In a 100 mL round bottom, one necked flask set up with a magnetic stir bar and a reflux condenser, 2-thiophene acetic acid (0.53 g, 3.69 mmol) was dissolved in acetic anhydride. The resulting solution was stirred at 60° C. for 15-20 min. Compound 3 (1.70 g, 5.53 mmol) was added followed by triethylamine (0.73 mL, 7.38 mmol) and the reaction mixture was stirred at 120° C. for 3 h. The reaction mixture was cooled to room temperature and poured into cold water. The liquid was decanted of and the crude oil was dissolved in DCM (100 mL). The organic phase was washed with water (2×100 mL), dried over sodium sulfate and solvent was removed under vacuum to give a crude oil. The crude oil was purified on a silica gel column with a gradient of hexanes/ethylacetate as eluent to yield the desired product, compound 4 as a dark orange solid. The yield was 0.54 g (35%)

Analysis: HNMR (CDCL3, 600 MHz) purity<98%. δ7.88 (s, 1H), 7.66 (dd, 1H, J=3.5, 1.2), 7.31 (d, 1H, J=8.6), 7.31 (dd, 1H, J=1.2), 7.08 (dd, 1H, J=5.1, 3.5), 6.59 (dd, 1H, J=8.9, 2.3), 6.50 (d, 1H, J=2.3), 4.13 (quartet, 2H, J=7.4), 3.43 (quartet, 2H, J=7.0), 3.32 (t, 2H, J=7.8), 2.33 (t, 2H, J=7.4), 1.73-1.61, m, 4H), 1.43-1.36 (m, 2H), 1.26 (t, 3H, J=7.4), 1.21 (t, 3H, J=7.0).

Example 5

6-(ethyl(2-oxo-3-(thiophen-2-yl)-2H-chromen-7-yl) amino) hexanoic acid, Compound 5

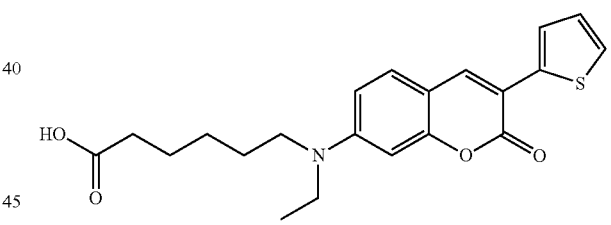

In a 10 mL round bottom, one necked flask set up with a magnetic stir bar, compound 4 (500 mg, 1.21 mmol) was dissolved in tetrahydrofuran (10 mL). Sodium hydroxide (242 mg, 6.05 mmol) was dissolved in water (10 mL) and the solutions were added together. The reaction mixture was stirred at room temperature for 5 h. Tetrahydrofuran was removed under vacuum and the aqueous phase was neutralized with aqueous hydrochloric acid (0.1M) to pH 7. The aqueous phase was then extracted with dichloromethane (2×50 mL), the combined organic phases were dried over sodium sulfate and solvent was removed under vacuum to give the crude oil. The crude oil was purified on a silica gel column with a gradient of hexanes/ethylacetate as eluent to yield the desired product, compound 5 as a dark orange solid. The yield was 140 mg (32%).

Analysis: HNMR (CDCl3, 600 MHz) purity (>95%). δ7.88 (s, 1H), 7.65 (dd, 1H, J=3.5, 1.2), 7.31 (d, 1H, J=8.6), 7.30 (dd, 1H, J=5.5, 1.2), 7.08 (dd, 1H, J=5.1, 3.5), 6.59 (dd, 1H, J=8.9, 2.3), 6.51 (d, 1H, J=2.3), 3.43 (quartet, 2H, J=7.0), 3.34 (t, 2H, J=7.8), 2.40 (t, 2H, J=7.4), 1.75-1.63 (m, 4H), 1.46-1.39 (m, 2H), 1.21 (t, 3H, J=7.0).

Example 6

Sodium 5-(7-((5-carboxypentyl)(ethyl)amino)-2-oxo-2H-chromen-3-yl)thiophene-2,4-disulfonate, Compound 6

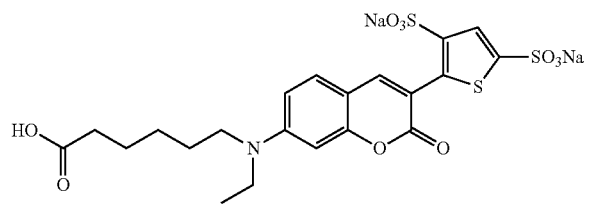

In a flame dried two necked round bottom flask set up with a magnetic stir bar and Argon inlet/Compound 5 (90 mg, 0.23 mmol) was dissolved in anhydrous DMF (5 mL). Sulfur trioxide dimethylformamide complex (1.49 g, 9.34 mmol) was added and the reaction mixture was stirred at 60° C. for 20 h under an inert Argon atmosphere. The reaction mixture was cooled to room temperature and quenched by addition of NaHCO$_3$ (saturated, 5 mL). Solvents where removed under vacuum to give the crude oil. The crude oil was purified on a reverse phase C18 column with a gradient of water/methanol as eluent to yield the desired product, as a dark orange oil. The obtained dark orange oil was then passed through a Sephadex LH20 column with an isocratic gradient of water as eluent to yield the desired product, compound 6 as a dark orange solid. The yield was 70 mg (55%)

Analysis: HNMR (D2O, 600 MHz) purity (>95%). δ8.78 (s, 1H), 7.34 (d, 1H, J=8.8), 7.21 (s, 1H), 6.71 (dd, 1H, J=8.4, 2.3), 6.52 (d, 1H, J=2.3), 3.45 (quartet, 2H, J=7.0), 3.34 (t, 2H, J=7.4), 1.89 (t, 1H, J=7.0), 1.58-1.52 (m, 2H), 1.52-1.47 (m, 2H), 1.33-1.28 (m, 2H), 1.13 (t, 3H, J=7.0).

Abs max=412 nm, Em max=507 nm
Mol. ext. coef=26000-27000 M-1cm-1
QY=0.70-0.75

Example 7

Sodium 5-(7-((6-((2,5-dioxopyrrolidin-1-yl)oxy)-6-oxohexyl)(ethyl)amino)-2-oxo-2H-chromen-3-yl)thiophene-2,4-disulfonate, Compound 7

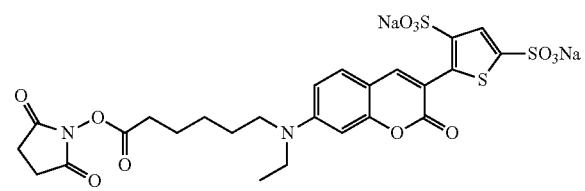

In a flame dried two necked round bottom flask set up with a magnetic stir bar and Argon inlet. Compound 6 (115 mg, 0.20 mmol) was dissolved in anhydrous DMF (5 mL). TSTU (65 mg, 0.22 mmol) and DHAP (26 mg, 0.22 mmol) were added. The reaction mixture was stirred at room temperature for 2 hours. The reaction mixture was drop wise added to diethyl ether (100 mL) under stirring. The resulting dark orange precipitate was collected by filtration and washed with diethyl ether (5 mL) and dichloromethane (5 mL). The dark orange solid was taken up in a minimal amount of anhydrous dimethylformamide, transferred into a 10 mL round bottom flask and concentrated under vacuum to yield the desired product, compound 7, as a dark orange solid. The yield was 120 mg (95%)

Analysis: mm (d6-DMSO, 600 MHz) purity (>95%). Spectrum is broadened δ8.74 (s, 1H), 7.33 (d, 1H, J=8.8), 7.21 (s, 1H), 6.71 (d, 1H, J=7.6), 6.50 (s, 1H), 3.44 (quartet, 2H, J=7.0), 3.34 (t, 2H, J=8.2), 2.71 (s, 4H), 2.67 (t, 2H, J=7.0), 1.67 (m, 2H), 1.58 (m, 2H), 1.41 (m, 2H), 1.11 (t, 3H, J=7.0).

Example 8

Sodium 5-(7-(ethyl(6-hydrazinyl-6-oxohexyl)amino)-2-oxo-2H-chromen-3-yl)thiophene-2,4-disulfonate, Compound 8

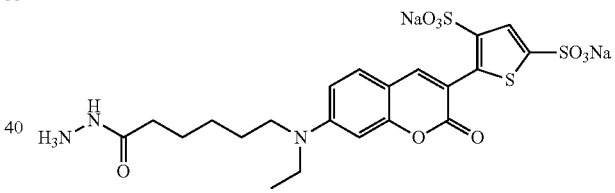

In a flame dried two necked round bottom flask set up with a magnetic stir bar and Argon inlet. Compound 7 (115 mg, 0.20 mmol) was dissolved in anhydrous DMF (0.55 mL). A solution of anhydrous hydrazine (125 μL, 4 mmol) in DMF (0.5 mL) was added and the reaction mixture was stirred at room temperature for 15 minutes. The reaction mixture was drop wise added to ethyl acetate (100 mM under stirring. The resulting dark orange precipitate was collected by filtration and washed with diethyl ether (5 mL) and dichloromethane (5 mL). The dark orange solid was taken up in a minimal amount of anhydrous dimethylformamide, transferred into a 10 mL round bottom flask and concentrated under vacuum to yield the desired product, compound 8, as a dark orange solid. The yield was 115 mg (91%)

Analysis: KNMR (d6-DMSO, 600 MHz) purity (>95%). Spectrum is broadened δ8.87 (s, 1H), 7.33 (d, 1H, J=8.8), 7.18 (s, 1H), 6.68 (d, 1H, J=7.6), 6.50 (s, 1H), 4.14 (bs, 2H), 3.44 (quartet, 2H, J=7.0), 3.34 (t, 2H, J=8.2), 2.19 (t, 2H, J=7.0), 1.67 (m, 2H), 1.58 (m, 2H), 1.41 (m, 2H), 1.11 (t, 3H, J=7.0).

Example 9

Sodium 5-(7-((6-((2-(2,5-dioxo-2,5-dihydro-1H-pyrrol-1-yl)ethyl)amino)-6-oxohexyl)(ethyl)amino)-2-oxo-2H-chromen-3-yl)thiophene-2, 4-disulfonate, Compound 9

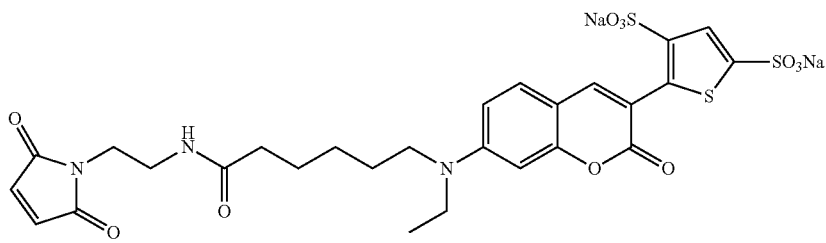

In a flame dried two necked round bottom flask set up with a magnetic stir bar and Argon inlet, Compound 7 (115 mg, 0.20 mmol) was dissolved in anhydrous DMF (2 mL). N-(2-Aminoethyl)maleimide trifluoroacetate salt was addend and the reaction mixture was stirred at room temperature for 2 hours. The reaction mixture was drop wise added to ethyl acetate (100 mL) under stirring. The resulting dark orange precipitate was collected by filtration and washed with diethyl ether (5 mL) and dichloromethane (5 mL). The dark orange solid was taken up in a minimal amount of anhydrous dimethylformamide, transferred into a 10 mL round bottom flask and concentrated under vacuum to yield the desired product, compound 9, as a dark orange solid. The yield was 115 mg (91%).

Analysis: mm (d6-DMSO, 600 MHz) purity (>95%). Spectrum is broadened δ8.87 (s, 1H), 7.86 (d, 2H, J=10.9), 7.33 (d, 1H, J=8.8), 7.18 (s, 1H), 6.68 (d, 1H, J=7.6), 6.50 (s, 1H), 3.66 (m, 2H), 3.44 (quartet, 2H, J=7.0), 3.34 (t, 2H, J=8.2), 2.19 (t, 2H, J=7.0), 1.67 (m, 2H), 1.58 (m, 2H), 1.41 (m, 2H), 1.11 (t, 3H, J=7.0).

Example 10

3-((6-ethoxy-6-oxohexyl)(3-hydroxyphenyl)amino) propane-1-sulfonic acid, Compound 10

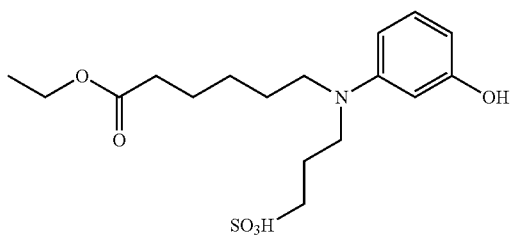 [SMILES: CCOC(=O)CCCCCN(CCCS(=O)(=O)O)c1cccc(O)c1]

In a 100 mL round bottom, one necked flask set up with a magnetic stir bar and a reflux condensor, compound 1 (2.85 g, 11.4 mmol) and 1,3-Propan Sultone (2.77 g, 22.69 mmol) were added under Argon. The reaction mixture was stirred at 100° C. overnight. The obtained crude oil was purified on a reverse phase C18 column with a gradient of Water/Methanol as eluent to yield the desired product, compound 10 as a colorless oil. The yield was 1.5 g (y=33%).

Analysis: HNMR (D2O, 600 MHz) purity>98%. δ7.34 (t, 1H, J=8.2), 6.92 (d, 1H, J=1.9), 6.90 (d, 1H, J=2.4), 6.90 (d, 1H, J=2.4), 3.96 (q, 2H, J=7.0), 3.59 (t, 2H, J=7.8), 3.44 (t, 2H, J=7.8), 2.75 (t, 2H, J=7.4), 2.15 (t, 2H, J=7.4), 1.81 (m, 2H), 1.43-1.23 (m, 4H), 1.15 (m, 2H), 1.07 (t, 3H, J=7.4).

Example 11

3-((6-ethoxy-6-oxohexyl)(4-formyl-3-hydroxyphenyl)amino) propane-1-sulfonic acid, Compound 11

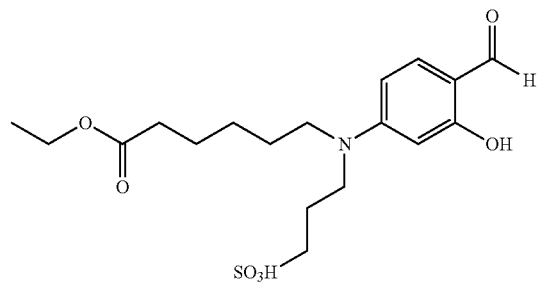 [SMILES: CCOC(=O)CCCCCN(CCCS(=O)(=O)O)c1ccc(C=O)c(O)c1]

A flame dried two necked 100 mL round bottom flask equipped with stir bar was cooled to 0° C. Anhydrous DMF (2 mL, 25.29 mmol) was added, followed by slow addition of POCl3 (1.17 mL, 12.65 mmol). The reaction mixture was then stirred at 0° C. for 30 min. and an additional 30 min. at room temperature. A solution of Compound 10 (1.0 g, 2.53 mmol) in DMF (anh, 5 mL) was slowly added at room temperature (RT) and the reaction mixture was stirred at RT for 20 h. The reaction mixture was cooled to 0° C. and quenched by addition of small pieces of ice at a time. The pH was neutralized to pH 8-10 with 1M NaOH. The aqueous solution was extracted with DCM (2×250 mL). Solvent was removed under vacuum to give a crude oil. The crude oil was purified on a reverse phase C18 column with a gradient of Water/Methanol as eluent to yield the desired product, compound 11 as a colorless oil. The yield was 500 mg (47%).

Analysis: HNMR (D2O, 600 MHz) purity>98%. δ9.29 (s, 1H), 7.32 (d, 1H, J=9.37), 6.30 (d, 1H, J=9.37), 5.96 (s, 1H), 3.99 (q, 2H, J=7.4), 3.41 (t, 2H, J=7.4), 3.29 (t, 2H, J=7.4), 2.81 (t, 2H, J=7.4), 2.23 (t, 2H, J=7.4), 1.92 (m, 2H), 1.49 (m, 2H), 1.21 (m, 2H), 1.08 (t, 3H, J=7.4).

Example 12

3-((6-ethoxy-6-oxohexyl)(2-oxo-3-(thiophen-2-yl)-2H-chromen-7-yl)amino)propane-1-sulfonic acid, Compound 12

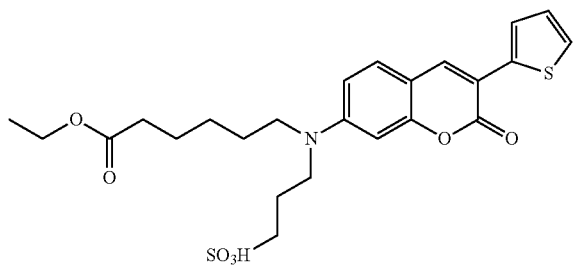 [SMILES: CCOC(=O)CCCCCN(CCCS(=O)(=O)O)c1ccc2cc(-c3cccs3)c(=O)oc2c1]

In a 100 mL round bottom, one necked flask set up with a magnetic stir bar and a reflux condenser, 2-thiophene acetic acid (167 mg, 1.18 mmol) was dissolved in acetic anhydride. The resulting solution was stirred at 60° C. for 15-20 min. Compound 11 (500 mg, 1.18 mmol) was added followed by triethylamine (0.31 mL, 2.24 mmol) and the reaction mixture was stirred at 120° C. for 3 h. The reaction mixture was cooled to room temperature and precipitated in Petroleum Ether. The dark oil wad decanted of and purified on a C18 column with a gradient of $H_2O$/MeOH as eluent to yield the desired product, compound 12 as a yellowish solid. The yield was 0.25 g (35%).

Analysis: HNMR (D2O, 400 MHz) purity>98%. δ7.53 (s, 1H), 7.34 (d, 1H, J=2.2), 7.22 (s, 1H), 6.83-6.75 (m, 2H), 6.24 (d, 1H, J=8.6), 6.18 (s, 1H), 4.03 (q, 2H, J=7.0), 3.30 (bs, 2H), 2.96 (bs, 2H) 2.87 (t, 2H, J=8.6), 2.15 (t, 2H, J=7.0) 1.98 (m, 2H), 1.40 (m, 2H), 1.15 (t, 2H, J=7.4), 0.9 (bs, 2H).

Example 13

6-((2-OXO-3-(thiophen-2-yl)-2H-chromen-7-yl)(3-sulfopropyl)amino) hexanoic acid, Compound 13

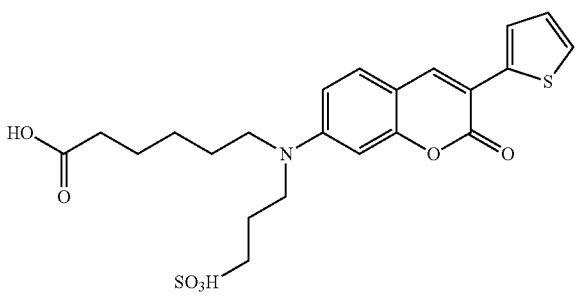 [SMILES: O=C(O)CCCCCN(CCCS(=O)(=O)O)c1ccc2cc(-c3cccs3)c(=O)oc2c1]

In a 10 mL round bottom, one necked flask set up with a magnetic stir bar, compound 12 (0.23 g, 0.43 mmol) was dissolved in tetrahydrofuran (5 mL). Sodium hydroxide (86 mg, 2.27 mmol) was dissolved in water (5 mL) and the solutions were added together. The reaction mixture was stirred at room temperature for 2 h. Tetrahydrofuran was removed under vacuum and the aqueous phase was neutralized with aqueous hydrochloric acid (0.1M) to pH 7. The crude oil was purified on a C18 column with a gradient of H2O/MeOH as eluent to yield the desired product, compound 13 as a yellowish solid. The yield was 130 mg (60%).

Analysis: HNMR (D2O, 400 MHz) purity>95%. δ7.87 (s, 1H), 7.47 (d, 1H, J=2.7), 7.45 (d, 1H, J=5.7), 7.25 (d, 1H, J=8.6), 7.15 (t, 1H, J=3.5), 6.62 (d, 1H, J=9.37), 6.37 (s, 1H), 3.38 (t, 2H, J=7.8), 3.26-3.15 (m, 2H), 2.94 (t, 2H, J=7.8), 2.23 (m, 2H, J=7.4), 2.02 (m 2H), 1.64-1.50 (m, 4H), 1.34 (m, 2H).

Example 14

Sodium 5-(7-((5-carboxypentyl)(3-sulfonatopropyl)amino)-2-oxo-2H-chromen-3-yl)thiophene-2,4-disulfonate, Compound 14

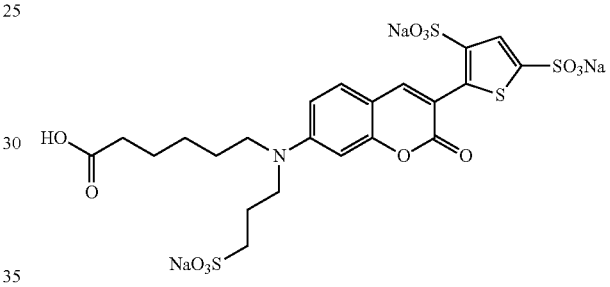

In a flame dried two necked round bottom flask set up with a magnetic stir bar and Argon inlet. Compound 13 (127 mg, 0.25 mmol) was dissolved in anhydrous DMF (5 mL). Sulfur trioxide dimethylformamide complex (1.55 g, 10 mmol) was added and the reaction mixture was stirred at 60° C. for 20 h under an inert Argon atmosphere. The reaction mixture was cooled to room temperature and quenched by addition of NaHCO3 (saturated, 5 mL). Solvents were removed under vacuum to give the crude oil. The crude oil was purified on a reverse phase C18 column with a gradient of water/methanol as eluent to yield the desired product, compound 14 as a yellowish solid. The obtained product was then passed through a Sephadex column LH20(3×40 cm, eluent H2O) with an isocratic gradient of water as eluent to yield the desired product, compound 14 as a yellowish solid. The yield was 75 mg (42%)

Analysis: HNMR (D2O, 400 MHz) purity>98%. δ8.07 (s, 1H), 7.56 (s, 1H), 7.41 (d, 1H, J=8.9), 6.76 (d, 1H, J=8.6), 6.62 (s, 1H), 3.49 (t, 2H, J=7.8), 3.36 (t, 2H, J=7.4), 2.86 (t, 2H, J=7.6), 2.07 (t, 2H, J=7.4), 1.97 (m, 2H), 1.56 (m, 2H), 1.48 (m 2H), 1.25 (m, 2H).

Abs max=414 nm, Em max=507 nm

Mol. ext. coef=26000-27000 $M^{-1}$ $cm^{-1}$

QY=0.70-0.75

Example 15

Sodium 5-(7-((6-((2,5-dioxopyrrolidin-1-yl)oxy)-6-oxohexyl)(3-sulfonatopropyl)amino)-2-oxo-2H-chromen-3-yl)thiophene-2,4-disulfonate, Compound 15

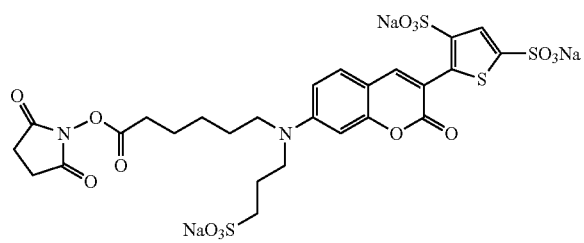

In a flame dried two necked round bottom flask set up with a magnetic stir bar and Argon inlet, Compound 14 (141 mg, 0.20 mmol) was dissolved in anhydrous DMF (5 mL). TSTU (65 mg, 0.22 mmol) and DMAP (26 mg, 0.22 mmol) were added. The reaction mixture was stirred at room temperature for 2 hours. The reaction mixture was drop wise added to diethyl ether (100 mL) under stirring. The resulting dark orange precipitate was collected by filtration and washed with diethyl ether (5 mL) and dichloromethane (5 mL). The dark orange solid was taken up in a minimal amount of anhydrous dimethylformamide, transferred into a 10 mL round bottom flask and concentrated under vacuum to yield the desired product, compound 15, as a dark orange solid. The yield was 143 mg (90%)

Analysis: HNMR (d6-DMSO, 600 MHz) purity (>95%). Spectrum is broadened δ8.07 (s, 1H), 7.56 (s, 1H), 7.41 (d, 1H, J=8.9), 6.76 (d, 1H, J=8.6), 6.62 (s, 1H), 3.43 (t, 2H, J=7.8), 3.36 (t, 2H, J=7.4), 2.86 (t, 2H, J=7.6), 2.71 (s, 4H), 2.67 (t, 2H, J=7.0), 1.97 (in, 2H), 1.56 (m, 2H), 1.48 (m 2H), 1.25 (m, 2H).

Example 16

2,5-dioxopyrrolidin-1-yl 6-(ethyl(2-oxo-3-(thiophen-2-yl)-2H-chromen-7-yl)amino)hexanoate, Compound 16

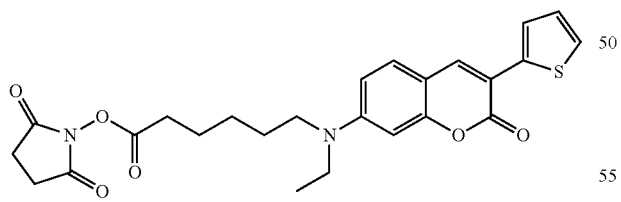

In a flame dried two necked round bottom flask set up with a magnetic stir bar and Argon inlet, Compound 5 (77 mg, 0.20 mmol) was dissolved in anhydrous DMF (5 mL). TSTU (65 mg, 0.22 mmol) and DMAP (26 mg, 0.22 mmol) were added. The reaction mixture was stirred at room temperature for 2 hours. The reaction mixture was drop wise added to cyclohexane (100 mL) under stirring. The resulting dark orange precipitate was collected by filtration and washed with cyclohexane 5 mL). The dark orange solid was taken up in a minimal amount of anhydrous dimethylformamide, transferred into a 10 mL round bottom flask and concentrated under vacuum to yield the desired product, compound 16, as a dark orange solid. The yield was 78 mg (90%)

Analysis: HNMR (d6-DMSO, 600 MHz) δ7.83 (s, 1H), 7.65 (dd, 1H, J=3.5, 1.2), 7.31 (d, 1H, J=8.6), 7.30 (dd, 1H, J=5.5, 1.2), 7.08 (dd, 1H, J=5.1, 3.5), 6.59 (dd, 1H, J=8.9, 2.3), 6.51 (d, 1H, J=2.3), 3.43 (quartet, 2H, J=7.0), 3.34 (t, 2H, J=7.8), 2.71 (s, 4H), 2.67 (t, 2H, J=7.0 Hz), 1.75-1.63 (m, 4H), 1.46-1.39 (m, 2H), 1.21 (t, 3H, J=7.0).

Example 17

Ethyl 6-(7-hydroxy-3,4-dihydroquinolin-1(2H)-yl) hexanoate, Compound 17

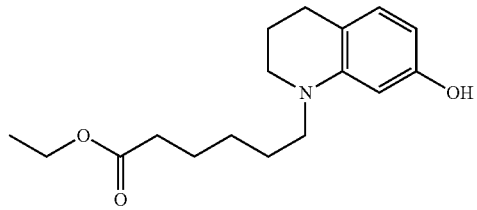 [SMILES: CCOC(=O)CCCCCN1CCCc2ccc(O)cc21]

In a 100 mL round bottom, one necked flask set up with a magnetic stir bar and a reflux condensor, 7-HydroxyQuinoline (10.0 g, 67.03 mmol) was dissolved in DMF. Ethyl-6-iodohexanoate (17.9 g, 80 mmol) was added. The reaction mixture was stirred at 50° C. for 20 h. Solvent was removed under vacuum to give a crude oil. The crude oil was purified on a silica gel column with a gradient of hexanes/ethylacetate as eluent to yield the desired product, compound 17 as a colorless oil. The yield was 13.7 g (74%).

Analysis: 1H NMR (CDCl3, 600 MHz): δ6.79 (d, 1H, J=8.0); 6.11 (bs, 2H); 4.14 (q, 2H, J=7.4); 3.27 (t, 2H, J=5.4); 3.20 (t, 2H, J=7.4) 2.67 (t, 2H, J=6.4); 2.32 (t, 2H, J=7.4); 1.92 (t, 2H, J=7.4) 1.72-1.56 (m; 4H); 1.36 (m, 2H); 1.25 (t, 3H, J=7.4)

Example 18 ethyl 6-(6-formyl-7-hydroxy-3,4-dihydroquinolin-1(2H)-yl)hexanoate, Compound 18

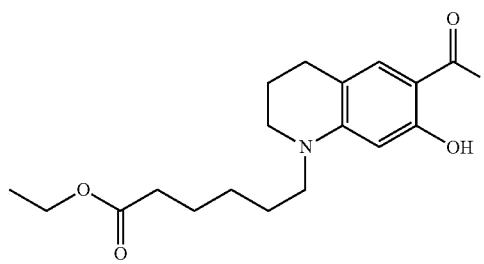

A flame dried two necked 1 L round bottom flask equipped with stir bar was cooled to 0° C. Anhydrous DMF (35 mL, 25.29 mmol) was added, followed by slow addition of FOCl3 (20.9 mL, 223 mmol). The reaction mixture was then stirred at 0° C. for 30 min. and an additional 30 min. at room temperature. A solution of Compound 17 (13.0 g, 44.6 mmol) in DMF (anh, 30 mL) was slowly added at room temperature (RT) and the reaction mixture was stirred at RT for 20 h. The reaction mixture was cooled to 0° C. and quenched by addition of small pieces of ice at a time. The pH was neutralized to pH 8-10 with 1M NaOH. The aqueous solution was extracted with DCM (2×400 mL). Solvent was removed under vacuum to give a crude oil. The crude oil was purified on a silica gel column with a gradient of hexanes/ethylacetate as eluent to yield the desired product, compound 18 as a colorless oil. The yield was 4.55 g (32%).

Analysis: HNMR (CDCl3, 600 MHz) purity>98%. δ11.60 (s, 1H; 9.43 (s, 1H); 6.94 (s, 1H); 5.98 (s, 1H); 4.14 (q, 2H, J=7.0); 3.36 (t, 2H, J=5.8); 3.28 (t, 2H, J=7.4); 2.67 (t, 2H, J=6.2); 2.32 (t, 2H, J=7.4); 1.91 (m, 2H; 1.65 (m, 2H); 1.38 (m, 2H); 1.26 (t, 3H, J=7.0).

Example 19

Ethyl 6-(2-oxo-3-(thiophen-2-yl)-7,8-dihydro-2H-pyrano[3,2-g]quinolin-9(6H)-yl)hexanoate, Compound 19

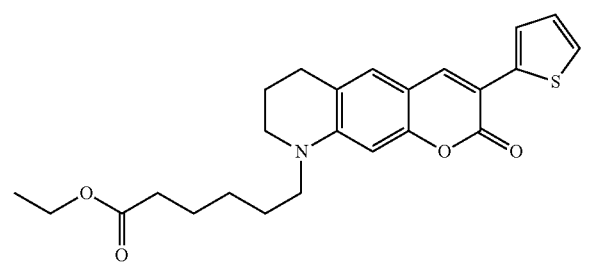 [SMILES: CCOC(=O)CCCCCN1CCCc2cc3cc(-c4cccs4)c(=O)oc3cc21]

In a 100 mL round bottom, one necked flask set up with a magnetic stir bar and a reflux condenser, 2-thiophene acetic acid (2.00 g, 14.11 mmol) was dissolved in acetic anhydride (20 ml). The resulting solution was stirred at 60° C. for 15-20 min. Compound 18 (4.5 g, 14.11 mmol) was added followed by triethylamine (3.73 mL, 26.80 mmol) and the reaction mixture was stirred at 120° C. for 3 h. The reaction mixture was cooled to room temperature, water was added. The organic material was extracted with EtOAc, dried over NaSO4, the solvent was evaporated and the crude material was purified on a silica gel column with a gradient of hexanes/ethylacetate as eluent to give an orange solid (2.1 g; y=35%), Analysis: HNMR (CDCL3, 400 MHz) purity>98%. δ7.39 (s, 1H), 7.21 (d, 1H, J=2.21), 7.08 (d, 1H, J=5.0), 6.83 (s, 1H), 6.06 (d, 1H, J=8.6), 6.02 (s), 4.14 (q, 2H), 3.27 (t, 2H); 3.20 (t, 2H) 2.67 (t, 2H); 2.32 (t, 2H); 1.92 (t, 2H) 1.72-1.56 (m; 4H); 1.36 (m, 2H); 1.25 (t, 3H).

Example 20

6-(2-oxo-3-(thiophen-2-yl)-7,8-dihydro-2H-pyrano[3,2-g]quinolin-9(6H)-yl)hexanoic acid, Compound 20

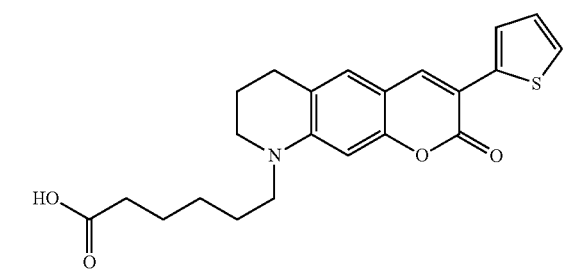 [SMILES: O=C(O)CCCCCN1CCCc2cc3cc(-c4cccs4)c(=O)oc3cc21]

In a 10 mL round bottom, one necked flask set up with a magnetic stir bar, compound 19(2.1 g, 4.93 mmol) was dissolved in tetrahydrofuran (5 mL). Sodium hydroxyl (986 mg, 24.65 mmol) was dissolved in water (10 mL) and the solutions were added together. The reaction mixture was stirred at room temperature for 2 h. Tetrahydrofuran was removed under vacuum and the aqueous phase was neutralized with aqueous hydrochloric acid (0.1M) to pH 7. The crude material was purified on a silica gel column with a gradient of hexanes/ethylacetate as eluent, compound 20 as a yellowish solid. The yield was 783 mg (40%).

Analysis: HNMR (CDCL3, 400 MHz) purity>98%. δ8.01 (s, 1H), 7.83 (s, 1H); 7.64 (dd, 1H, J=3.5, 1.2), 7.30 (d, 1H, J=5.8); 7.08 (dd, 1H, J=4.7, 3.5), 7.03 (s, 1H), 3.48 (t, 2H, J=5.2);); 3.38 (t, 2H, J=5.8) 2.78 (t, 2H, J=6.5); 1.96 (m, 2H) 1.72-1.56 (m; 4H); 1.41 (m, 2H).

Example 21

Sodium 5-(9-(5-carboxypentyl)-2-oxo-6,7,8,9-tetrahydro-2H-pyrano[3,2-g]quinolin-3-yl)thiophene-2,4-disulfonate, Compound 21

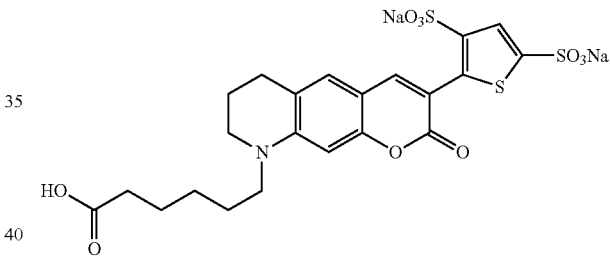

In a flame dried two necked round bottom flask set up with a magnetic stir bar and Argon inlet. Compound 20 (780 mg, 1.97 mmol) was dissolved in anhydrous DMF (20 mL). Sulfur trioxide dimethylformamide complex (12.07 g, 78.88 mmol) was added and the reaction mixture was stirred at 60° C. for 20 h under an inert Argon atmosphere. The reaction mixture was cooled to room temperature and quenched by addition of NaHCO3 (saturated). Solvents where removed under vacuum to give the crude oil. The crude oil was purified on a reverse phase C18 column with a gradient of water/methanol as eluent to yield the desired product, compound 21 as a yellowish solid. The obtained product was then passed through a Sephadex column LH20 (3×40 cm, eluent H2O) with an isocratic gradient of water as eluent to yield the desired product, compound 21 as a yellowish solid. The yield was 403 mg (34%)

Analysis: HNMR (D2O, 400 MHz) purity>98%. δ8.14 (s, 1H), 7.69 (s, 1H), 7.21 (s, 1H); 6, 6.59 (s, 1H), 3.35-3.25 (m, 4H) 2.77 (t, 2H, J=5.8); 2.24 (t, 2H, J=7.8) 1.92 (m, 2H); 1.72-1.56 (m; 4H); 1.36 (m, 2H).

Example 22

Sodium 5-(9-(6-((2,5-dioxopyrrolidin-1-yl)oxy)-6-oxohexyl)-2-oxo-6,7,8,9-tetrahydro-2H-pyrano[3,2-g]quinolin-3-yl)thiophene-2,4-disulfonate, Compound 22

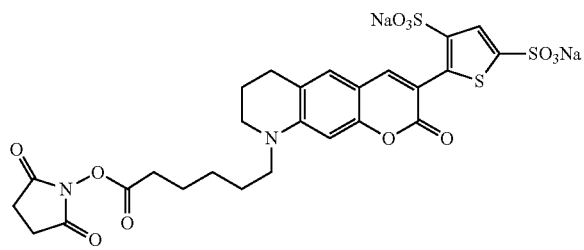

In a flame dried two necked round bottom flask, set up with a magnetic stir bar and Argon inlet, Compound 21 (350 mg, 0.58 mmol) was dissolved in anhydrous DMF (5 ml). TSTU (209 mg, 0.70 mmol) and DMAP (84 mg, 0.70 mmol) were added. The reaction mixture was stirred at room temperature for 2 hours. The reaction mixture was drop wise added to diethyl ether (100 mL) under stirring. The resulting dark orange precipitate was collected by filtration and washed with diethyl ether (10 mL) and dichloromethane (10 mL). The dark orange solid was taken up in a minimal amount of anhydrous dimethylformamide, transferred into a 10 mL round bottom flask and concentrated under vacuum to yield the desired product as a dark orange solid. The yield was mg (283 mg; 70%) Analysis: HNMR (DMSO, 400 MHz) purity>98%. δ8.07 (s, 1H), 7.56 (s, 1H), 6.76 (S, 1H), 6.62 (8, 1H), 3.27 (t, 2H); 3.20 (t, 2H) 2.67 (t, 2H); 2.73 (s, 4H); 2.32 (t, 2H); 1.92 (m, 2H) 1.72-1.56 (m; 4H); 1.36 (m, 2H).

Example 23

Sodium 5-(7-((5-carboxypentyl)(ethyl)amino)-2-oxo-2H-chromen-3-yl)thiophene-2 sulfonate, Compound 23

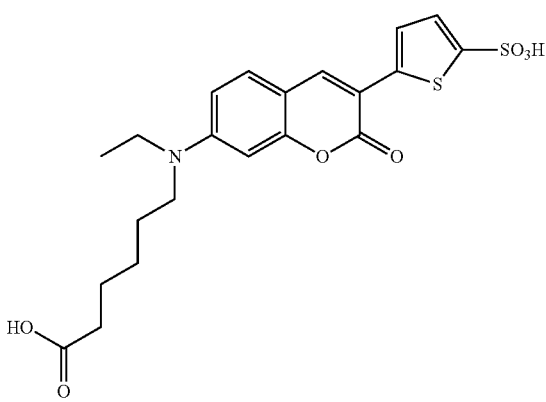 [SMILES: CCN(CCCCCC(=O)O)c1ccc2cc(-c3ccc(S(=O)(=O)O)s3)c(=O)oc2c1]

In a flame dried two necked round bottom flask set up with a magnetic stir bar and Argon inlet, Compound 5 (90 mg, 0.23 mmol) was dissolved in anhydrous DMF (5 mL). Sulfur trioxide dimethylformamide complex (0.75 g, 4.65 mmol) was added and the reaction mixture was stirred at 60° C. for 20 h under an inert Argon atmosphere. The reaction mixture was cooled to room temperature and quenched by addition of NaHCO3 (saturated, 5 mL). Solvents where removed under vacuum to give the crude oil. The crude oil was purified on a reverse phase C18 column with a gradient of water, methanol as eluent to yield the desired product, as a dark orange oil. The obtained dark orange oil was then passed through a Sephadex LH20 column with an isocratic gradient of water as eluent to yield the desired product, compound 6 as a dark orange solid. The yield was 85 mg (73%)

Analysis: HNMR (D2O, 600 MHz) purity (>95%). δ7.26 (s, 1H), 7.38 (d, 1H, J=3.9), 7.16 (d, 1H, J=3.9), 7.00 (d, 1H, J=9.0), 6.40 (d, 1H, J=10.5), 6.12 (s, 1H), 3.54 (q, 2H, J=7.1), 3.46 (t, 2H, J=7.7), 2.21 (t, 2H, J=7.7), 1.69 (m, 2H, 1.63 (m, 2H), 1.39 (m, 2H, 1.21 (t, 3H, J=6.6).

Abs max=441 nm, Em max=518 nm
Mol. ext. coef=26000-27000 M-1 cm-1
QY=0.70-0.75

Example 24

Absorption and Emission Spectra for Compounds 6, 14 and 23

Figure 2:
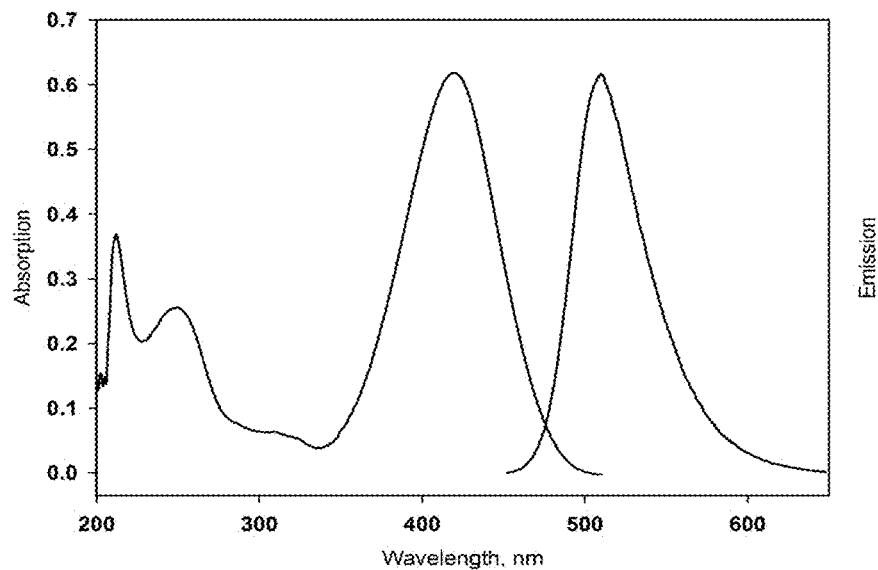
FIG. 2 shows the normalized absorption and emission spectra of compound 6 in PBS buffer (pH8.5).

Compound was diluted in PSB buffer at pH 8.4. The absorption spectrum was measured in a 1 cm cuvette on a UV-Spectrophotometer Varian Cary 100 Bio. The emission spectrum was measured in a 1 cm cuvette on a Spectrofluorometer Varian Cary Eclipse. The absorption and emission spectra of compound 6 were normalized and are shown in FIG. 2. The spectra show an optimal fitting of the $Abs_{max}$ with the 405 nm violet excitation source and a large Stokes shift, demonstrating the usefulness in multiplex applications.

Example 25

Determination of Molar Extinction Coefficient

An accurately weighed sample of compound (6) was dissolved in a measured amount of water to give a stock solution of known concentration (C=mg/mL). The stock solution was serially diluted over an appropriate range by dilution factors (D) in PBS. The absorption spectra were measured in a 1 cm cuvette on a Varian spectrophotometer. The absorption maxima (Amax) were determined. The molecular weight (MW) of compound 6 was derived from the structure of example 6.

The molar extinction coefficient (ε) was calculated from the following equation:

$$\varepsilon = (A\max \cdot D \cdot MW)/C$$

The molar extinction coefficient of compound 6 was found to be 26000 $M^{-1}$ $cm^{-1}$.

Example 26

Fluorescence Quantum Yield

Fluorescent quantum yield of compound 6 was determined using fluorescein as reference standard. Compound 6 was serially diluted in 10 mM sodium phosphate buffer with absorption at 400 nm and 427 nm≤0.10. Fluorescein was serially diluted in 0.1 mM sodium hydroxide. Absorptions of all serial dilutions were measured in 1 cm cuvettes on an UV-VIS Varian-Cary 100 BIO spectrophotometer. Corrected emission spectra were recorded on a Varian Eclipse spectrofluorometer in 1 cm cuvettes with excitation at 427 nm for all samples. Data were plotted as total fluorescence integral against the absorbance and analysed using Sigma plot software. The quantum yield of compound 6 was calculated using the following formula:

$$QY = QY_{std} \times (Em_{sample}/Em_{std}) \times (Abs_{std} \times Abs_{sample})$$

Where QY is the quantum yield. $QY_{std}$ is the known quantum yield of fluorescein. $Em_{sample}$ and $Abs_{sample}$ are the measured fluorescence emission and absorption of compound 6. $Em_{std}$ and $Abs_{std}$ are the measured fluorescence emission and absorption of fluorescein.

The Quantum Yield of compound (6) was determined to be 0.7±0.1.

Example 27 pH Dependency of Dye Fluorescence

Samples of compound 6 were prepared over a range of pH values at equal final concentrations in appropriate aqueous solutions (acq HCl for pH 1 and 2; 50 mM potassium phosphate for pH 3 to 8.5; 50 mM sodium bicarbonate for pH 9 to 10 and acq NaOH for pH 12).

Measurements of fluorescence emission were performed at 1 pH unit intervals from pH 1 to pH 8 and pH12 on a Varian Eclipse spectrofluorometer in 1 cm cuvettes with excitation at 4.17 nm for all samples and fluorescence emission was measured at 510 nm.

The pH dependency curve for compound (6) is shown in FIG. 3 and demonstrates completely pH independence between pH values 4 and 12.

Example 28

Preparation of Protein Dye Conjugates

Polyclonal Goat anti-Mouse antibody (AbNova Cod. PAB9347) was diluted to a concentration of 2 mg/mL in 10 mM PBS buffer. The solution was aliquoted into eight sample vials of each 125 µL to which were added 25 µL of a sodium bicarbonate buffer (pH 9.6). The N-hydroxy succinimidyl ester compound (7) was dissolved in anhydrous DMSO and the concentration was determined spectrophotometrically. Calculated amounts, ranging from 10-100 molar equivalents, of compound 7 with respect to antibody were added to each antibody sample aliquot. The reaction mixtures were incubated at room temperature in the dark for 1 hour. Non reacted dye excess was removed from the reaction mixtures by separation on a Sephadex G25 column and all samples of isolated dye-conjugates were analyzed for dye to protein ratio (D/P ratio) and concentration. The obtained D/P ratios were then plotted against the molar equivalents of dye used and are shown in FIG. 4.

Figure 5:
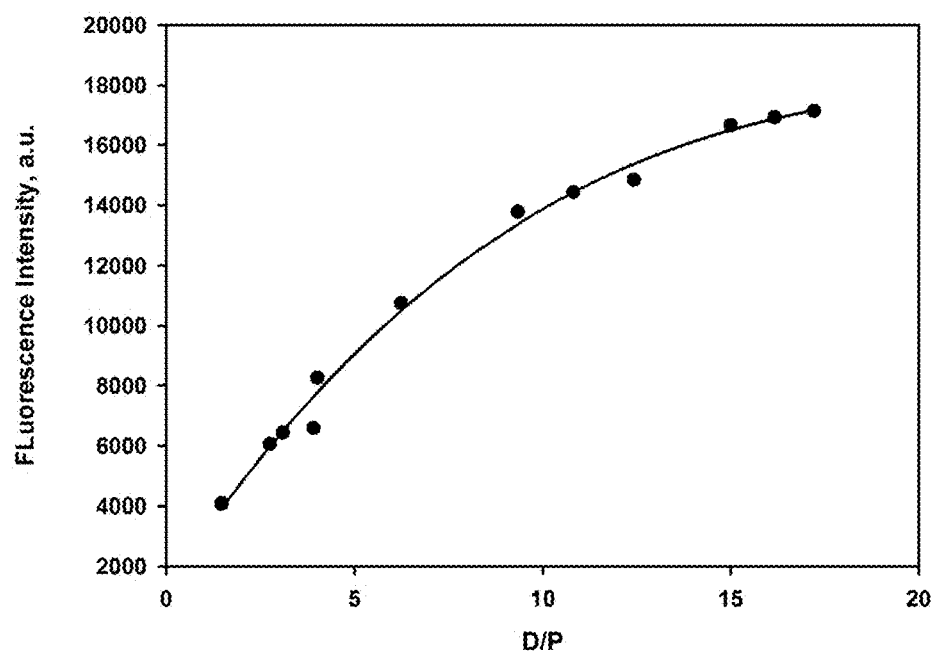
FIG. 5 shows a plot of the fluorescence data obtained using dye conjugates of secondary goat anti-mouse antibodies conjugated to compound 7 over a range of dye-to-protein ratios.

Next, the fluorescence of each sample was measured at equal antibody concentration (abs 238 nm) and the obtained total fluorescence values were plotted against the corresponding D/P ratios and are shown in FIG. 5.

Figure 4:
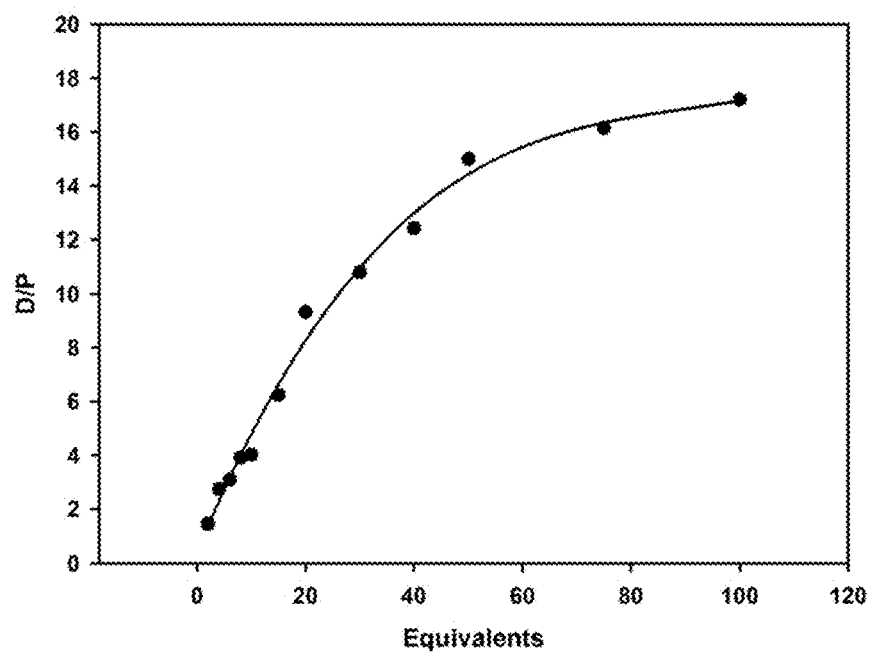
FIG. 4 shows a plot of the dye to protein ratios obtained by conjugation of secondary goat anti-mouse antibodies with increasing molar excess of compound 7.

FIGS. 4 and 5 demonstrate high labelling efficiency and excellent fluorescent quantum yield over a wide range of D/P ratios.

Goat anti-mouse-compound 16 was prepared as described above. The total fluorescence of conjugate Goat anti-mouse-compound 16 was compared to Goat anti-mouse-compound 7 by measuring the total fluorescence integral (total emission band) at equal antibody concentration and equal D/P ratio with excitation at 420 nm, (FIG. 9a, 9b), showing a three times higher fluorescence for the di-sulfonated conjugate Goat anti-mouse-compound 7 in comparison to the non-sulfonated conjugate Goat anti-mouse-compound 16.

Example 29

CD4 and CD19 Antibody Conjugations

Figure 6A:
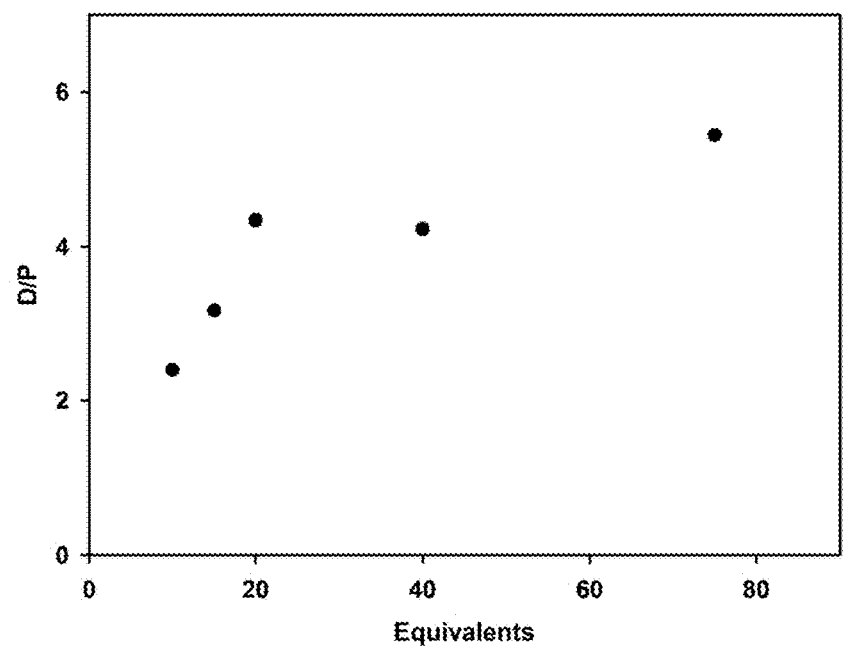
FIGS. 6a and 6b show a plot of the dye to protein ratios obtained by conjugation of mouse anti-human CD4 (FIG. 6a) and mouse anti-human CD19 (FIG. 6b) antibodies with increasing molar excess of compound 7.
Figure 6B:
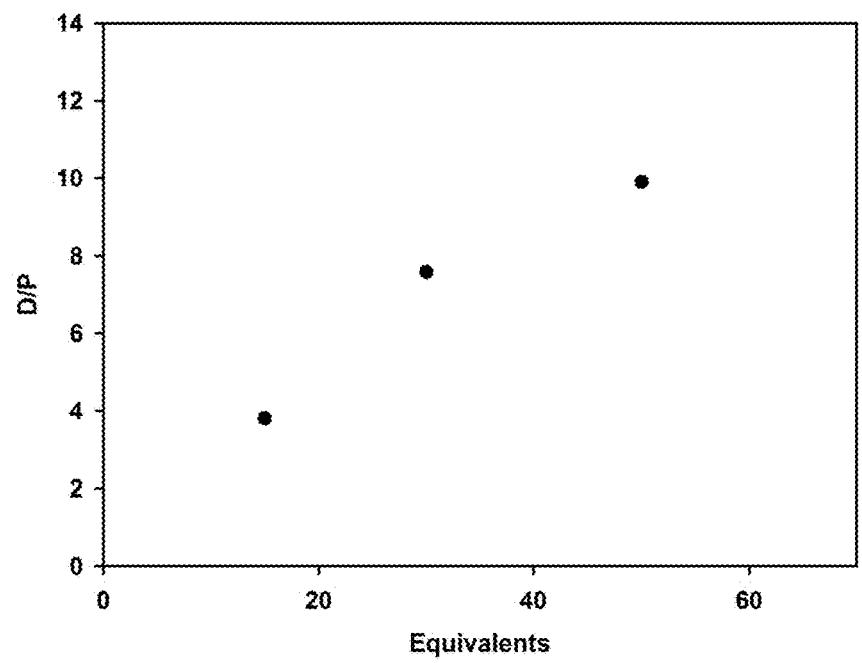

Purified Mouse anti-human CD4 antibody (clone SK3) was purchased from Biolegend (cod. 344602). Mouse anti-human CD8 (clone RPA-T8, cod. 555364), Mouse anti-human CD4 (clone RFA-T4, cod. 300502) and Mouse anti-human CD19 (clone HIB19, cod. 555410) antibodies as well as the corresponding BD Horizon V500 labeled antibodies: V500-Anti Human CD4 (clone: RPA-T4, cod. 560769), V500-Anti Human CD19 (clone HIB19(RUO), cod. 561125) and V500-Anti Human CD8 clone (clone RPA-T8, cod. 560775) were purchased from BD Bioscience. Purified antibodies were supplied at a 0.5 mg/mL concentration. As described above, conjugations were performed in order to assess optimal D/P ratios and are shown in FIGS. 6a and 6b.

The dye/protein ratios used in the labeling reactions, at various protein concentrations, produced conjugates with different dye to protein ratios as shown in table 3 for each dye/protein pair.

TABLE 3

| Protein | Protein concentration | Dye compound Nr | D/P ratio |
|---|---|---|---|
| Mouse anti-human CD4 clone SK3 | 0.5 mg/mL | 7 | 3.8, 7.6, 9.9 |
| Mouse anti-human CD19 clone HIB19 | 0.5 mg/mL | 7 | 2.4, 3.2, 4.3, 4.2, 5.4 |
| Mouse anti-human CD19 clone HIB19 | 2.0 mg/mL | 7 | 10.0 |
| Mouse anti-human CD8 clone RPA-T8 | 0.5 mg/mL | 7 | 2.6, 4.8, 8.3, 11.0 |

Figure 7A:
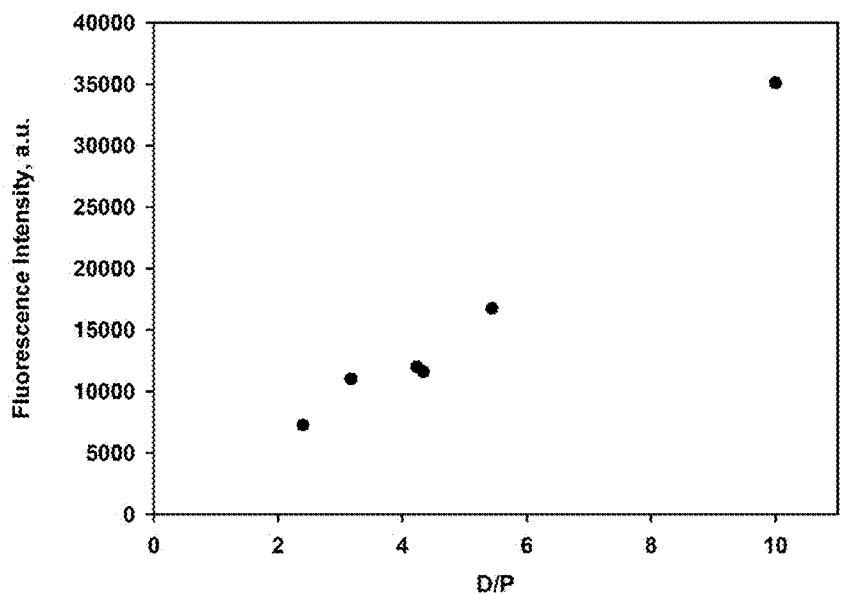
FIGS. 7a and 7b show a plot of the fluorescence data obtained using dye conjugates of mouse anti-human CD4 (FIG. 7a) and mouse anti-human CD19 (FIG. 7b) antibodies conjugated to compound 7 over a range of dye-to-protein ratios.
Figure 7B:
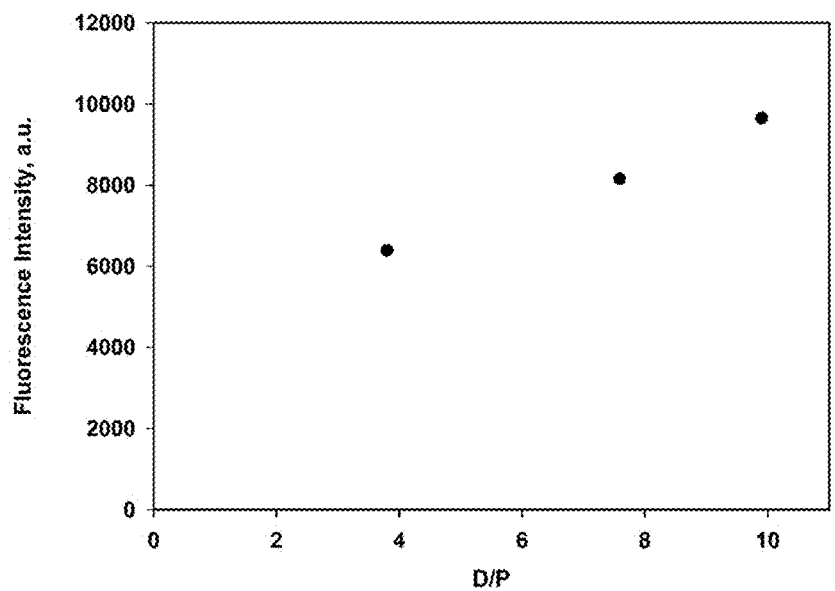

Fluorescence of each sample was measured at equal antibody concentration (abs 280 nm) and the obtained total fluorescence were plotted against the corresponding D/P ratios (FIGS. 7a and 7b).

Figure 8A:
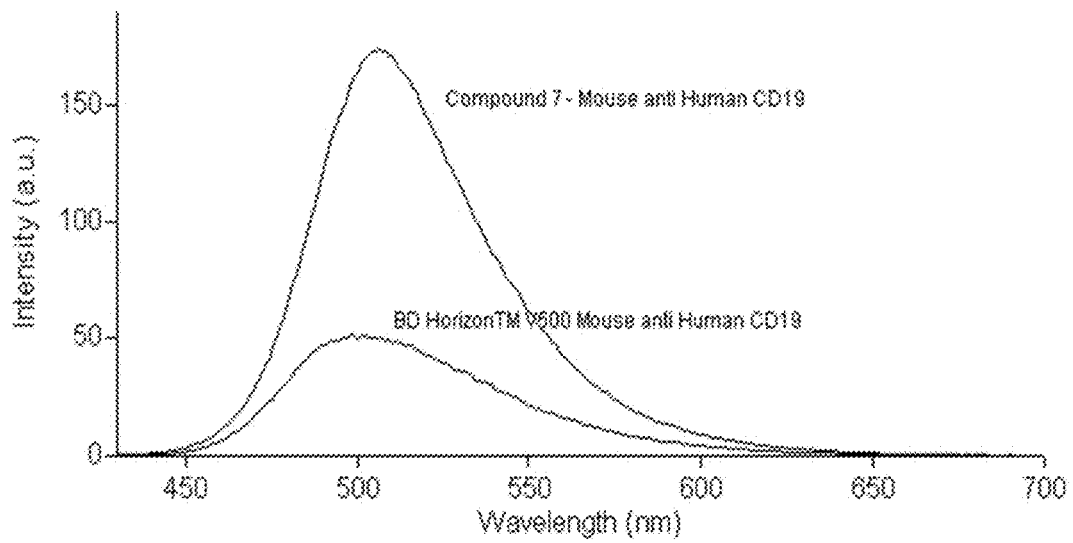
FIGS. 8a and 8b show full emission spectra (FIG. 8a) and integrated fluorescence intensity histogram (FIG. 8b) for a mouse anti-human CD19 antibody labeled with either Compound 7 and BD Bioscience Horizon V500 at equal antibody concentration and dye-to-protein ratio when excited at 420 nm.
Figure 8B:
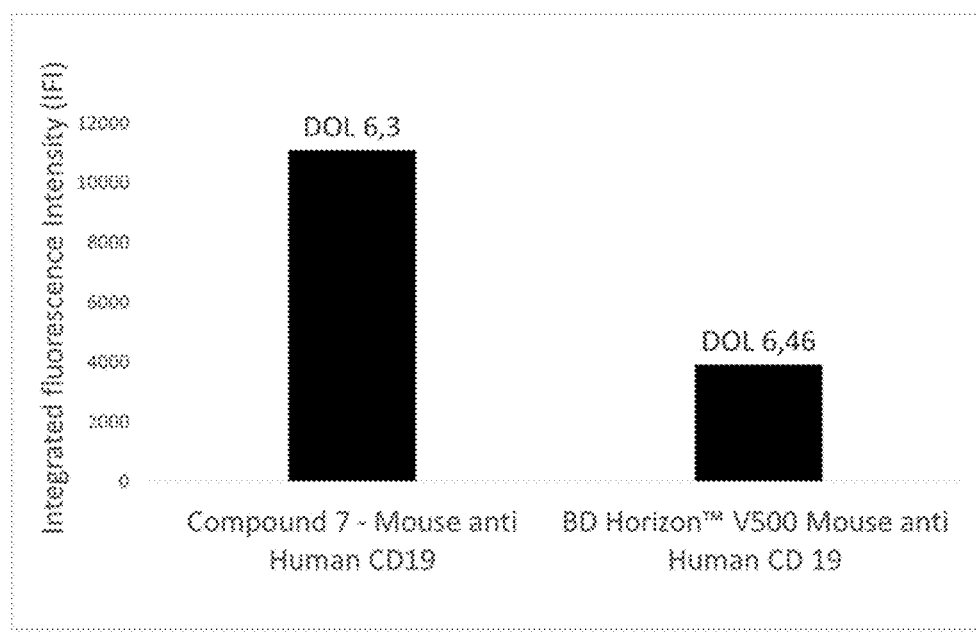

Subsequently, the total fluorescence of conjugates Mouse anti-human CD19-compound 7 was compared to Mouse anti-human CD19-V500 by measuring the total fluorescence integral (total emission band) at equal antibody concentration and equal D/P ratio with excitation at 420 nm. FIGS. 8a and 8b show a three times higher fluorescence for dye compound 7 conjugate of the present invention in comparison to the BD Horizon V500 dye conjugate.

Example 30

Cell Analysis by Flow Cytometry Ising Dye-Antibody Conjugates

MAVKR-1 cells were purchased from ATCC (cod. ATCC® CRL-3008™), unless specified otherwise. Cell lines propagated in suspension cultures were grown in RPMI1640 medium supplemented with 10% FBS.

PBMC were isolated from buffy coats by Ficoll-Hypaque standard density gradient technique. Buffy coat of human blood from healthy donor was obtained from the Blood Bank C.R.S. (Centro Regionale Sangue), Ospedale Maagiore—Largo Nigrisoli, 2—40133 Bologna, Itlay.

Sample of 10^6 cells were stained with dye-conjugate for 15-30 minutes at +4° C. in the dark at a dye-conjugate quantity of 30 ng for peripheral blood lymphocytes (FIG. 8) and 5 ug for MAVER-1 (FIG. 9) per test in staining buffer (0.5% BSA in D-PBS). Following staining, the sample was washed (adding 1 ml of staining buffer) twice, re-suspended with D-PBS and held at 4° C. in the dark until flow cytometric acquisition. Acquisition of the stained cells was carried out using a BD FACS ARIAXI (BD Biosciences, San Jose, Calif.) equipped with a blue (488 nm), a red (633 nm), and a violet (405 nm) laser. The detection optics includes a 530/30 filter. The flow cytometer was setup following the manufacturer's instructions, including a Cytometer and Setup Tracking to obtain the best identification of bright populations and the best resolution of dim populations. Flow cytometric acquisition of sample of stained cells was performed according to the manufacture's protocols, and the data was analyzed excluding doublet using a pulse geometry gate (FSC-W×FSC-A) to obtain fluorescence intensity for the cell population of interest.

It will be understood that methods for preparing antibody conjugates used and particular reaction conditions used can affect the result of assay. Routine experimentation and titration should be carried with cells and reagents that mimic each experimental conditions to determinate optimal staining condition.

Figure 10:
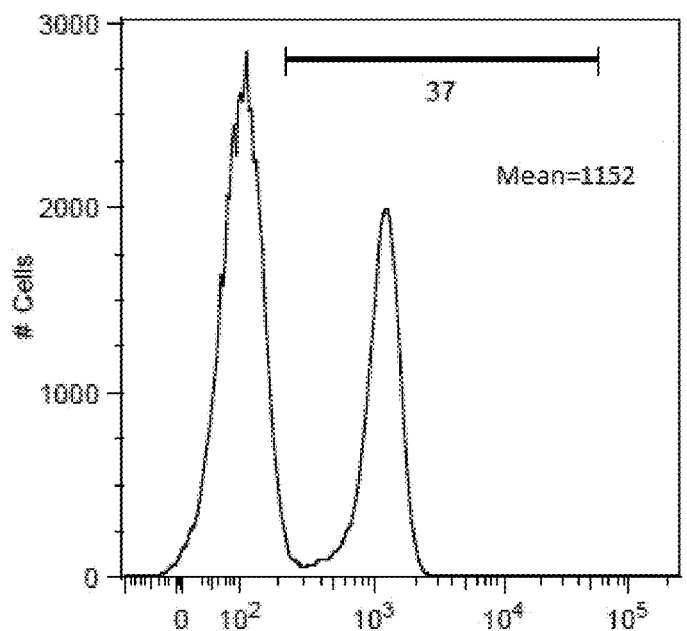
FIG. 10 shows the expression of human CD4 in lymphocytes from healthy donor in flow cytometry using mouse anti-human CD4-compound 7 conjugate.

FIG. 10 shows the expression of mouse anti-human CD4 antibody in lymphocytes from healthy donor in flow cytometry using mouse anti-human CD4-compound 7 conjugate.

Figure 11:
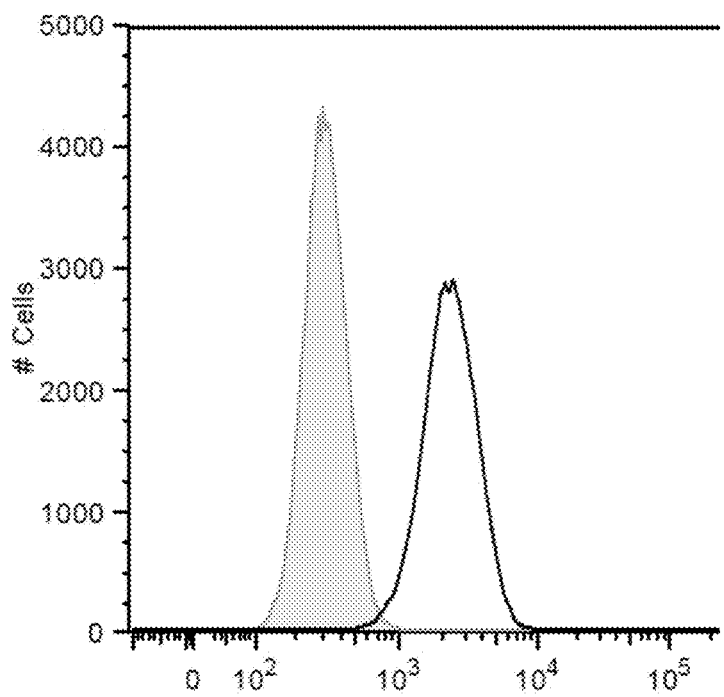
FIG. 11 shows MAVER-1 cells line stained with mouse anti-human CD19-compound 7 conjugate (white filled histogram) and unstained (grey filled histogram).

FIG. 11 shows MAVER-1 cells line stained with mouse anti-human CD19-compound 7 conjugate (white filled histogram) and unstained (grey filled histogram). The results indicate that the dye-conjugates of the present invention are useful in preparing antigen specific detection reagents for immunofluorescence assays analyzed by flow cytometry. In one or more embodiments, a 7-amino-3-thienyl coumarin dye may have formula (I):

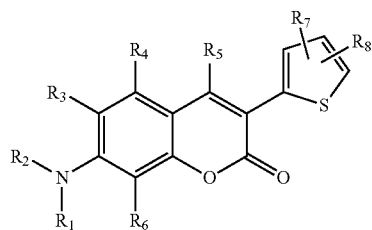

(I)

wherein
R1 is L-RG;
R2, R3, R4, R5, and R6 are independently selected from H, halogen, cyano, trifluoromethyl, WSG, L-WSG, substituted or unsubstituted alkyl and substituted or unsubstituted alkoxy;
R7 and R8 are WSG;
RG is a chemically reactive group selected from carboxylic acid, an activated ester of a carboxylic acid, sulfonyl halide, acyl halide, acrylamide, amine, aldehyde sulfonate ester, anhydride, azide, haloacetamide, halotriazine, hydrazine, hydroxylamine, isocyanate, isothiocyanate, maieimide, phosphoramidate and alkyne;
L is a linker of formula (VI):

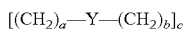

$[(CH_2)_a-Y-(CH_2)_b]_c$ (VI)

wherein
Y is the same or different and is selected from none, O, S, NK, NR9, $SO_2$—NH, $SO_2$—NR9, CO—NH, CO—O, CO—S, 1,3-triazole, aminotriazine, triazinyl ether, NH—CO—NH, NH—CS—NH, NH—CO—O, O—POR9-O, $SO_2$—O, amino acid, aryl or heteroaryl;
wherein R9 is alkyl or WSG;
a and c can be the same or different and are an integer number 1 to 10, and
b is an integer number 0 to 10;
WSG is a water soluble group selected from sulfonic acid, sulfate, alkyl sulfonic acid, sulfonamide, phosphate, phosphonic acid, boronic acid, ammonium, pyridinium, monosaccharide and —$(CH_2$—$CH_2$—$O)_x$ in which x is an integer number from 1 to 10;
and salts thereof.

In one or more embodiments, the substituent moiety present either on the alkyl or alkoxy is selected from hydroxy, halogen, alkylsulfonamido, cyano, azide, WSG or heteroaryl. More preferably the substituent moiety present either on the alkyl or alkoxy is selected from hydroxy, halogen, alkylsulfonamido, cyano, azide, or heteroaryl.

In one or more embodiments, a 7-amino-3-thienyl coumarin dye may have formula (II):

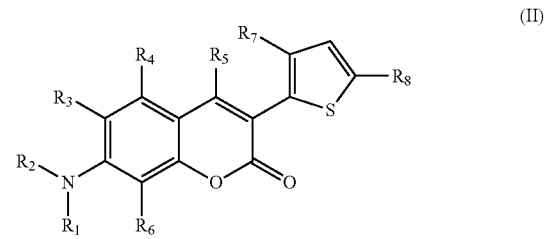

(II)

wherein
R1 is L-RG;
R2, R3, R4, R5, and R6 are independently selected from H, halogen, cyano, trifluoromethyl, WSG, L-WSG, substituted or unsubstituted alkyl, and substituted or unsubstituted alkoxy;
R7 and R8 are sulfonic acid;
RG is a chemically reactive group selected from carboxylic acid, an activated ester of a carboxylic acid, sulfonyl halide, acyl halide, acrylamide, amine, aldehyde sulfonate ester, anhydride, azide, haloacetamide, halotriazine, hydrazine, hydroxylamine, isocyanate, isothiocyanate, maieimide, phosphoramidate and alkyne;
L is a linker of formula (VI):

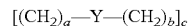

$[(CH_2)_a-Y-(CH_2)_b]_c$ (VI)

wherein
Y is the same or different and is selected from none, O, S, NH, NR9, $SO_2$—NH, $SO_2$—NR9, CO—NH, CO—O, CO—S, 1,3-triazole, aminotriazine, triazinyl ether, MH—CO—NH, NH—CS—NH, MH—CO—O, O—POR9-O, $SO_2$—O, amino acid, aryl or heteroaryl;
WSG is a water soluble group selected from sulfonic acid, sulfate, alkyl sulfonic acid, sulfonamide, phosphate, phosphonic acid, boronic acid, ammonium, pyridinium, monosaccharide and —$(CH_2$—$CH_2$—$O)_x$ in which x is an integer number from 1 to 10;
and salts thereof.

In one or more embodiments, a 7-amino-3-thienyl coumarin dye may have formula (III):

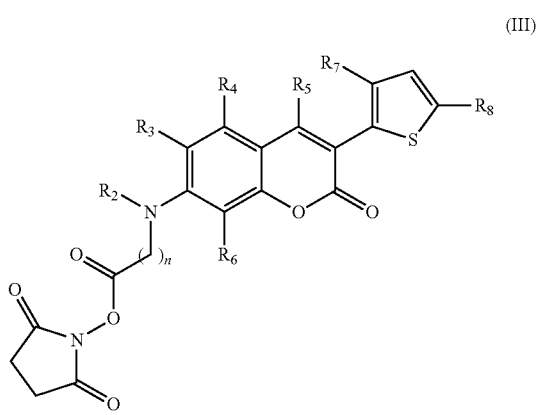

(III)

wherein
R2 is selected from substituted or unsubstituted alkyl, and L-WSG;
R3, R4, R5, R6 are H;
L is a linker of formula (VI):

[(CH$_2$)$_a$—Y—(CH$_2$)$_b$]$_c$     (VI)

wherein
Y is the same or different and is selected from none, O, S, m, NR9, SO$_2$—NH, SO$_2$—NR9, CO—NH, CO—O, CO—S, 1,3-triazole, aminotriazine, triazinyl ether, NH—CO—NH, NH—CS—NH, NH—CO—O, O—POR9-O, SO$_2$—O, amino acid, aryl or heteroaryl;
WSG is a water soluble group selected from sulfonic acid, sulfate, alkyl sulfonic acid, sulfonamide, phosphate, phosphonic acid, boronic acid, ammonium, pyridinium, monosaccharide and —(CH$_2$—CH$_2$—O)$_x$ in which x is an integer number from 1 to 10;
n is an integer number 1 to 10;
R7 and R8 are sulfonic acid;
and salts thereof.

In one or more embodiments, a 7-amino-3-thienyl coumarin dye may have formula (IV):

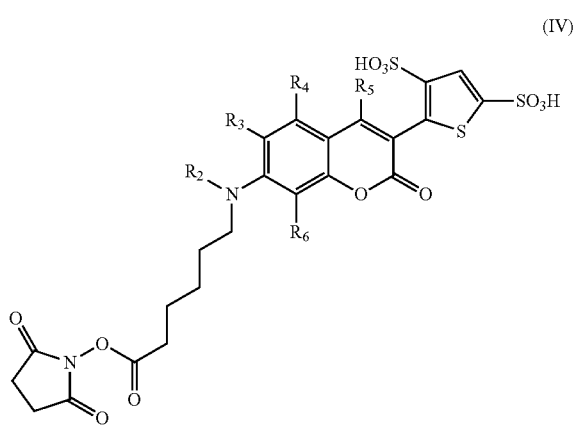

(IV)

wherein
R2 is selected from substituted or unsubstituted alkyl, and L-WSG;
R3, R4, R5, R6 are H;
L is a linker of formula (VI):

[(CH$_2$)$_a$—Y—(CH$_2$)$_b$]$_c$     (VI)

wherein
Y is the same or different and is selected from none, O, S, NH, NR9, SO$_2$—NH, SO$_2$—NR9, CO—NH, CO—O, CO—S, 1,3-triazole, aminotriazine, triazinyl ether, NH—CO—MH, NH—CS—NH, NH—CO—O, O—POR9-O, SO$_2$—O, amino acid, aryl or heteroaryl;
WSG is a water soluble group selected from sulfonic acid, sulfate, alkyl sulfonic acid, sulfonamide, phosphate, phosphonic acid, boronic acid, ammonium, pyridinium, monosaccharide and —(CH$_2$—CH$_2$—O)$_x$ in which x is an integer number from 1 to 10;
and salts thereof.

In one or more embodiments, in a 7-amino-3-thienyl coumarin dye of formula (I), (II), (III) or (IV), Y may be selected from none, O, S, SO$_2$—NH, SO$_2$—NR9, CO—NH, CO—O, CO—S, 1,3-triazole, NH—CO—NH, NH—CS—NH, NH—CO—O, SO$_2$—O, aryl, heteroaryl and amino acid, preferably Y is selected from none, O, S, SO$_2$—NH, SO$_2$—NR9, CO—NH, CO—O and 1,3-triazole, wherein wherein R9 is alkyl or WSG, being WSG a water soluble group selected from sulfonic acid, sulfate, alkyl sulfonic acid, sulfonamide, phosphate, phosphonic acid, boronic acid, ammonium, pyridinium, monosaccharide and —(CH$_2$—CH$_2$—O)$_x$ in which x is an integer number from 1 to 10.

In one or more embodiments, in a 7-amino-3-thienyl coumarin dye of formula (I), (II), (III) or (IV), WSG may be selected from sulfonic acid, alkyl sulfonic acid, sulfonamide, phosphate, phosphonic acid, ammonium, pyridinium, cyclodextrin, monosaccharide, oligosaccharide, dextrane and —(CH$_2$—CH$_2$—O)$_x$ in which x is an integer number from 1 to 10, preferably WSG is selected from sulfonic acid, alkyl sulfonic acid, sulfonamide, ammonium and —(CH2-CH2-O)x in which x is an integer number from 1 to 10.

In one or more embodiments, in a 7-amino-3-thienyl coumarin dye of formula (I), (II), (III) or (IV), RG may be selected from carboxylic acid, an activated ester of a carboxylic acid, sulfonyl halide, acyl halide, amine, alkyl or aryl halide, anhydride, azide, haloacetamide, halotriazine, hydrazine, isocyanate, isothiocyanate, maieimide, phosphoramidate, thiol, alcohol and alkyne, preferably RG is selected from carboxylic acid, an activated ester of a carboxylic acid, amine, azide, haloacetamide, hydrazine, isocyanate, maieimide and alkyne.

In one or more embodiments, the 7-amino-3-thienyl coumarin dye of formula (I) may be selected from:
sodium 5-(7-((5-carboxypentyl)(ethyl)amino)-2-oxo-2H-chromen-3-yl)thiophene-2,4-disulfonate;
sodium 5-(7-((6-((2,5-dioxopyrrolidin-1-yl)oxy)-6-oxohexyl)(ethyl)amino)-2-oxo-2H-chromen-3-yl)thiophene-2,4-disulfonate;
sodium 5-(7-(ethyl(6-hydrazinyl-6-oxohexyl)amino)-2-oxo-2H-chromen-3-yl)thiophene-2,4-disulfonate;
sodium 5-(7-((6-((2-(2,5-dioxo-2,5-dihydro-1H-pyrrol-1-yl)ethyl)amino)-6-oxohexyl)(ethyl)amino)-2-oxo-2H-chromen-3-yl)thiophene-2,4-disulfonate;
sodium 5-(7-((6-((2,5-dioxopyrrolidin-1-yl)oxy)-6-oxohexyl)(3-sulfonatopropyl)amino)-2-oxo-2H-chromen-3-yl)thiophene-2,4-disulfonate;
sodium 5-(9-(6-((2, 5-dioxopyrrolidin-1-yl) oxy)-6-oxohexyl)-2-oxo-6,7,8,9-tetrahydro-2H-pyrano[3,2-g]quinolin-3-yl)thiophene-2,4-disulfonate;
5-(7-((6-((2,5-dioxcpyrrolidin-1-yl)oxy)-6-oxohexyl)(2-(2-methoxyethoxy)ethyl)amino)-2-oxo-2H-chromen-3-yl)thiophene-2,4-disulfonic acid;

5-(7-((6-((2,5-dioxopyrrolidin-1-yl)oxy)-6-oxohexyl)(2-oxo-2-((3-sulfopropyl)amino)ethyl)amino)-2-oxo-2H-chromen-3-yl)thiophene-2,4-disulfonic acid;

5-(7-((6-((2,5-dioxopyrrolidin-1-yl)oxy)-6-oxohexyl)(3-(N-(2-sulfoethyl)sulfamoyl)propyl)amino)-2-oxo-2H-chromen-3-yl)thiophene-2,4-disulfonic acid;

5-(7-((3-(N-(6-((2,5-dioxopyrrolidin-1-yl)oxy)-6-oxohexyl)sulfamoyl)propyl)(ethyl)amino)-2-oxo-2H-chromen-3-yl)thiophene-2,4-disulfonic acid;

5-(7-((4-(((2,5-dioxopyrrolidin-1-yl)oxy)carbonyl)benzyl)(ethyl)amino)-2-oxo-2H-chromen-3-yl)thiophene-2,4-disulfonic acid.

In one or more embodiments, a 7-amino-3-thienyl coumarin dye conjugate may have formula (V):

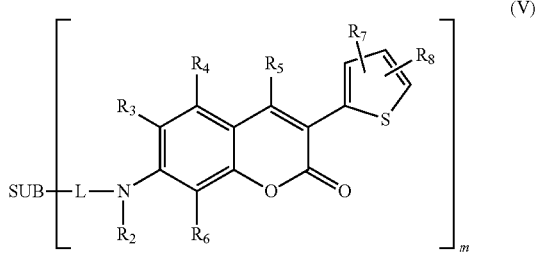

(V)

wherein

R2, R3, R4, R5, and R6 are independently selected from H, halogen, cyano, trifluoromethyl, WSG, L-WSG, substituted or unsubstituted alkyl and substituted or unsubstituted alkoxy;

R7 and R8 are sulfonic acid;

L is a linker of formula (VI):

(VI)

wherein Y is the same or different and is selected from none, O, S, NH, NR9, SO$_2$—NH, SO$_2$—NR9, CO—NH, CO—O, CO—S, 1,3-triazole, aminotriazine, triazinyl ether, NH—CO—NH, NH—CS—NH, NH—CO—O, O—POR9-O, SO$_2$—O, amino acid, aryl and heteroaryl, wherein R9 is alkyl or WSG, a and c can be the same or different and are an integer number 1 to 10, and b is an integer number 0 to 10;

WSG is a water soluble group and is selected from sulfonic acid, sulfate, alkyl sulfonic acid, sulfonamide, phosphate, phosphonic acid, boronic acid, ammonium, pyridinium, monosaccharide and —(CH$_2$—CH$_2$—O)$_x$ in which x is an integer number from 1 to 10;

m is an integer number 1 to 25;

SUB is an amino acid, a peptide, a protein, a saccharide, a nucleoside, a nucleotide, an oligonucleotide, a nucleic acid, a hapten, a drug or a lipid;

and salts thereof.

In one or more embodiments, in a 7-amino-3-thienyl coumarin dye conjugate of formula (V), R2 and R3 may be bound to the thienyl ring in positions 2 and 4, and may be sulfonic acid groups or salts thereof.

In one or more embodiments, a 7-amino-3-thienyl coumarin dye conjugate may have formula (V), R3, R4, R5 and R6 may be hydrogen atoms.

In one or more embodiments, in the 7-amino-3-thienyl coumarin aye conjugate of formula (V), R2 may be substituted or unsubstituted alkyl or L-WSG;

L may be a linker as defined above;

WSG may be a water soluble group as defined above.

In one or more embodiments, a kit may comprise at least one 7-amino-3-thienyl coumarin dye of formula (I), (II), (III) or (IV).

In one or more embodiments, a kit may comprise at least one 7-amino-3-thienyl coumarin dye conjugate of formula (V).

In one or more embodiments, a 7-amino-3-thienyl coumarin dye may have formula (II):

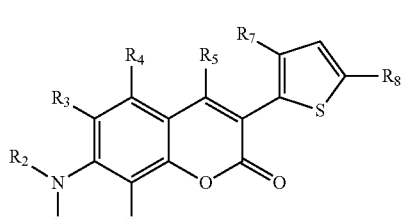

(II)

wherein

R1 is L-RG;

R2, R3, R4, R5, and R6 are independently selected from H, halogen, cyano, trifluoromethyl, WSG, L-WSG, substituted or unsubstituted alkyl and substituted or unsubstituted alkoxy;

R7 and R8 are WSG;

RG is a chemically reactive group selected from carboxylic acid, an activated ester of a carboxylic acid, sulfonyl halide, acyl halide, acrylamide, amine, aldehyde sulfonate ester, anhydride, azide, haloacetamide, halotriazine, hydrazine, hydroxylamine, isocyanate, isothiocyanate, maieimide, phosphoramidate and alkyne;

L is a linker of formula (VI):

(VI)

wherein

Y is the same or different and is selected from none, O, S, NH, NRS, SO$_2$—NH, SO$_2$—NR9, CO—NH, CO—O, CO—S, 1,3-triazole, aminotriazine, triazinyl ether, NH—CO—NH, NH—CS—NH, NH—CO—O, O—POR9-O, SO$_2$—O, amino acid, aryl or heteroaryl, wherein R9 is alkyl or WSG, a and c can be the same or different and are an integer number 1 to 10, and b is an integer number 0 to 10;

WSG is a water soluble group selected from sulfonic acid, sulfate, alkyl sulfonic acid, sulfonamide, phosphate, phosphonic acid, boronic acid, ammonium, pyridinium, monosaccharide and —(CH$_2$—CH$_2$—O)$_x$ in which x is an integer number from 1 to 10;

and salts thereof.

In one or more embodiments, a 7-amino-3-thienyl coumarin dye may have formula (III):

(III)

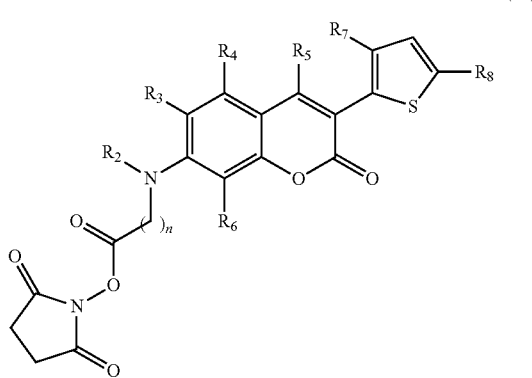

wherein
R2 is selected from substituted or unsubstituted alkyl, and L-WSG;
R3, R4, R5, R6 are H;
R7 and R3 are sulfonic acid;
L is a linker of formula (VI):

$$[(CH_2)_a—Y—(CH_2)_b]_c \quad (VI)$$

wherein
Y is the same or different and is selected from none, O, S, NH, NR9, SO$_2$—NH, SO$_2$—NR9, CO—NH, CO—O, CO—S, 1,3-triazole, aminotriazine, triazinyl ether, NH—CO—NH, NH—CS—NH, NH—CO—O, O—POR9-O, SO$_2$—O, amino acid, aryl or heteroaryl,
wherein R9 is alkyl or WSG;
WSG is a water soluble group selected from sulfonic acid, sulfate, alkyl sulfonic acid, sulfonamide, phosphate, phosphonic acid, boronic acid, ammonium, pyridinium, monosaccharide and —(CH$_2$—CH$_2$—O)$_x$ in which x is an integer number from 1 to 10;
n is an integer number 1 to 10;
and salts thereof.

In one or more embodiments, a 7-amino-3-thienyl coumarin dye may have formula (IV):

(IV)

wherein
R2 is selected from substituted or unsubstituted alkyl, and L-WSG;
R3, R4, R5, R6 are H;
L is a linker as defined in claim 1;

WSG is a water soluble group selected from sulfonic acid, sulfate, alkyl sulfonic acid, sulfonamide, phosphate, phosphonic acid, boronic acid, ammonium, pyridinium, monosaccharide and —(CH$_2$—CH$_2$—O)$_x$ in which x is an integer number from 1 to 10;
and salts thereof.

In one or more embodiments, in a 7-amino-3-thienyl coumarin dye of formula (II), (III) or (IV), Y may be selected from none, O, S, SO$_2$—NH, SO$_2$—NR9, CO—NH, CO—O, CO—S, 1,3-triazole, NH—CO—NH, NH—CS—NH, NH—CO—O, SO$_2$—O, aryl, heteroaryl and amino acid, preferably Y is selected from none, O, S, SO$_2$—NH, SO$_2$—NR9, CO—NH, CO—O and 1,3-triazole, wherein R9 is alkyl or WSG; and wherein WSG is a water soluble group selected from sulfonic acid, sulfate, alkyl sulfonic acid, sulfonamide, phosphate, phosphonic acid, boronic acid, ammonium, pyridinium, monosaccharide and —(CH$_2$—CH$_2$—O)$_x$ in which x is an integer number from 1 to 10.

In one or more embodiments, in a 7-amino-3-thienyl coumarin dye of formula (II), (III) or (IV), WSG may be selected from sulfonic acid, alkyl sulfonic acid, sulfonamide, phosphate, phosphonic acid, ammonium, pyridinium, cyclodextrin, monosaccharide, oligosaccharide, dextrane and —(CH$_2$—CH$_2$—O)$_x$ in which x is an integer number from 1 to 10, preferably WSG is selected from sulfonic acid, alkyl sulfonic acid, sulfonamide, ammonium and —(CH$_2$—CH$_2$—O)$_x$ in which x is an integer number from 1 to 10

In one or more embodiments, in a 7-amino-3-thienyl coumarin dye of formula (II), (III) or (IV), RG may be selected from carboxylic acid, an activated ester of a carboxylic acid, sulfonyl halide, acyl halide, amine, alkyl or aryl halide, anhydride, azide, haloacetamide, halotriazine, hydrazine, isocyanate, isothiocyanate, maieimide, phosphoramidate, thiol, alcohol and alkyne, preferably RG is selected from carboxylic acid, an activated ester of a carboxylic acid, amine, azide, haloacetamide, hydrazine, isocyanate, maieimide and alkyne.

In one or more embodiments, a 7-amino-3-thienyl coumarin dye of formula (II), (III) or (IV) may be selected from:
sodium 5-(7-((5-carboxypehtyl)(ethyl)amino)-2-oxo-2H-chromen-3-yl)thiophene-2, 4-disulfonate;
sodium 5-(7-((6-((2,5-dioxopyrrolidin-1-yl)oxy)-6-oxohexyl)(ethyl)amino)-2-oxo-2H-chromen-3-yl)thiophene-2,4-disulfonate;
sodium 5-(7-(ethyl(6-hydrazinyl-6-oxohexyl)amino)-2-oxo-2H-chromen-3-yl)thiophene-2, 4-disulfonate;
sodium 5-(7-((6-((2-(2,5-dioxo-2,5-dihydro-1H-pyrrol-1-yl)ethyl)amino)-6-oxohexyl)(ethyl)amino)-2-oxo-2H-chromen-3-yl)thiophene-2, 4-disulfonate;
sodium 5-(7-((6-((2, 5-dioxopyrrolidin-1-yl)oxy)-6-oxohexyl)(3-sulfonatopropyl)amino)-2-oxo-2H-chromen-3-yl)thiophene-2,4-disulfonate;
sodium 5-(9-(6-((2,5-dioxopyrrolidin-1-yl)oxy)-6-oxohexyl)-2-oxo-6,7,8,9-tetrahydro-2H-pyrano[3,2-g]quinolin-3-yl)thiophene-2, 4-disulfonate;
5-(7-((6-((2,5-dioxopyrrolidin-1-yl)oxy)-6-oxohexyl)(2-(2-methoxyethoxy)ethyl)amino)-2-oxo-2H-chromen-3-yl)thiophene-2,4-disulfonic acid;
5-(7-((6-((2,5-dioxopyrrolidin-1-yl)oxy)-6-oxohexyl)(2-oxo-2-((3-sulfopropyl)amino)ethyl)amino)-2-oxo-2H-chromen-3-yl)thiophene-2,4-disulfonic acid;
5-(7-((6-((2,5-dioxopyrrolidin-1-yl)oxy)-6-oxohexyl)(3-(N-(2-sulfoethyl)sulfamoyl)propyl)amino)-2-oxo-2H-chromen-3-yl)thiophene-2,4-disulfonic acid;
5-(7-((3-(N-(6-((2,5-dioxopyrrolidin-1-yl)oxy)-6-oxohexyl)sulfamoyl)propyl)(ethyl)amino)-2-oxo-2R-chromen-3-yl)thiophene-2,4-disulfonic acid;

5-(7-((4-(((2,5-dioxopyrrolidin-1-yl)oxy)carbonyl) benzyl)(ethyl)amino)-2-oxo-2H-chromen-3-yl)thiophene-2,4-disulfonic acid.

In one or more embodiments, a 7-amino-3-thienyl coumarin dye conjugate may have formula (V):

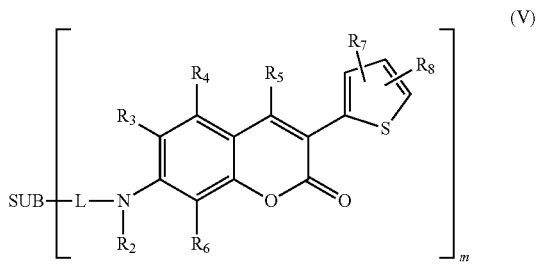

(V)

wherein

R2, R3, R4, R5, and R6 are independently selected from H, halogen, cyano, trifluoromethyl, WSG, L-WSG, substituted or unsubstituted alkyl and substituted or unsubstituted alkoxy;

R7 and R8 are a sulfonic acid and are bound to the thienyl ring in positions 2 and 4;

L is a linker of formula (VI):

(VI)

wherein Y is the same or different and is selected from none, O, S, NH, NR9, $SO_2$—NH, $SO_2$—NR9, CO—NH, CO—O, CO—S, 1,3-triazole, aminotriazine, triazinyl ether, NH—CO—NH, NH—CS—NH, NH—CO—O, O—POR9-O, $SO_2$—O, amino acid, aryl and heteroaryl, wherein R9 is alkyl or WSG, a and c can be the same or different and are an integer number 1 to 10, and b is an integer number 0 to 10;

WSG is a water soluble group and is selected from sulfonic acid, sulfate, alkyl sulfonic acid, sulfonamide, phosphate, phosphonic acid, boronic acid, ammonium, pyridinium, monosaccharide and —$(CH_2—CH_2—O)_x$ in which x is an integer number from 1 to 10;

m is an integer number 1 to 25;

SUB is an amino acid, a peptide, a protein, a saccharide, a nucleoside, a nucleotide, an oligonucleotide, a nucleic acid, a hapten, a drug or a lipid;

and salts thereof.

In one or more embodiments, in a 7-amino-3-thienyl coumarin dye conjugate having formula (V), R3, R4, R5 and R6 may be hydrogen atoms.

In one or more embodiments, in a 7-amino-3-thienyl coumarin dye conjugate having formula (V), R2 may be substituted or unsubstituted alkyl or L-WSG;

L is a linker of formula (VI):

(VI)

wherein Y is the same or different, and is selected from none, O, S, NH, NR9, $SO_2$—NH, $SO_2$—NR9, CO—NH, CO—O, CO—S, 1,3-triazole, aminotriazine, triazinyl ether, NH—CO—NH, NH—CS—NH, NH—CO—O, O—POR9-O, $SO_2$—O, amino acid, aryl and heteroaryl, wherein R9 is alkyl or WSG, a and c can be the same or different and are an integer number 1 to 10, and b is an integer number 0 to 10;

WSG is a water soluble group and is selected from sulfonic acid, sulfate, alkyl sulfonic acid, sulfonamide, phosphate, phosphonic acid, boronic acid, ammonium, pyridinium, monosaccharide and —$(CH_2—CH_2—O)_x$ in which x is an integer number from 1 to 10.

In one or more embodiments, a kit may comprise at least one 7-amino-3-thienyl coumarin dye of formula (II), (III), or (IV) as defined above.

In one or more embodiments, a kit may comprise at least one 7-amino-3-thienyl coumarin dye conjugate of formula (V).

In one or more embodiments, a 7-amino-3-thienyl coumarin dye may have formula (II):

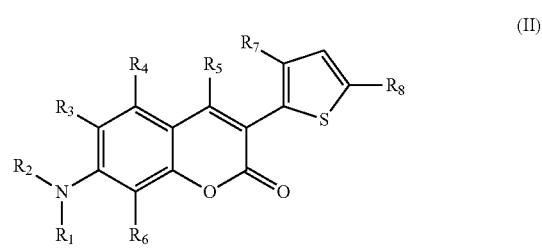

(II)

wherein

R1 is L-RG;

R2 is selected from substituted or unsubstituted alkyl, and L-WSG;

R3, R4, R5, and R6 are independently selected from H, halogen, cyano, trifluoromethyl, WSG, L-WSG, substituted or unsubstituted alkyl and substituted or unsubstituted alkoxy;

R7 and R8 are WSG;

RG is a chemically reactive group selected from carboxylic acid, an activated ester of a carboxylic acid, sulfonyl halide, acyl halide, acrylamide, amine, aldehyde, sulfonate ester, anhydride, azide, haloacetamide, halotriazine, hydrazine, hydroxylamine, isocyanate, isothiocyanate, maieimide, phospboramidate and alkyne;

L is a linker of formula (VI):

(VI)

wherein

Y is the same or different and is selected from none, O, S, NH, NR9, $SO_2$—NH, $SO_2$—NR9, CO—NH, CO—O, CO—S, 1,3-triazole, aminotriazine, triazinyl ether, NH—CO—NH, NH—CS—NH, NH—CO—O, O—POR9-O, $SO_2$—O, amino acid, aryl or heteroaryl, wherein R9 is alkyl or WSG, a and c can be the same or different and are an integer number 1 to 10, and b is an integer number 0 to 10;

WSG is a water soluble group selected from sulfonic acid, sulfate, alkyl sulfonic acid, sulfonamide, phosphate, phosphonic acid, boronic acid, ammonium, pyridinium, monosaccharide and —$(CH_2—CH_2—O)_x$ in which x is an integer number from 1 to 10;

and salts thereof.

In one or more embodiments, a 7-amino-3-thienyl coumarin dye may have formula (III):

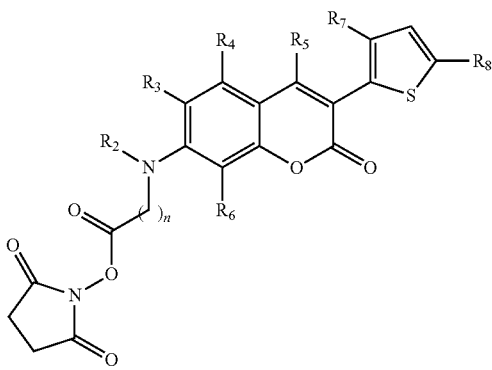

wherein
R2 is selected from substituted or unsubstituted alkyl, ana L-WSG;
R3, R4, R5, R6 are H;
R7 and R3 are sulfonic acid;
L is a linker of formula (VI):

$$[(CH_2)_a—Y—(CH_2)_b]_c \qquad (VI)$$

wherein
Y is the same or different and is selected from none, O, S, NH, NR9, SO$_2$—NH, SO$_2$—NR9, CO—NH, CO—O, CO—S, 1,3-triazole, aminotriazine, triazinyl ether, NH—CO—NH, NH—CS—NH, NH—CO—O, O—POR9-O, SO$_2$—O, amino acid, aryl or heteroaryl,
wherein R9 is alkyl or WSG,
a and c can be the same or different and are an integer number 1 to 10, and
b is an integer number 0 to 10;
WSG is a water soluble group selected from sulfonic acid, sulfate, alkyl sulfonic acid, sulfonamide, phosphate, phosphonic acid, boronic acid, ammonium, pyridinium, monosaccharide and —(CH$_2$—CH$_2$—O)$_x$ in which x is an integer number from 1 to 10;
and salts thereof.
In one or more embodiments, a 7-amino-3-thienyl coumarin dye may have formula (IV):

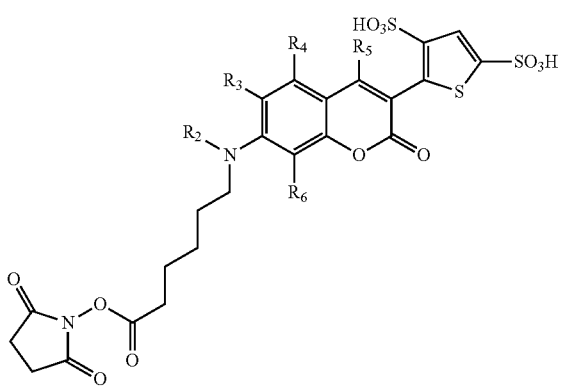

wherein
R2 is selected from substituted or unsubstituted alkyl, and L-WSG;
R3, R4, R5, R6 are H;

L is a linker of formula (VI):

$$[(CH_2)_a—Y—(CH_2)_b]_c \qquad (VI)$$

wherein
Y is the same or different and is selected from none, O, S, NH, NR9, SO$_2$—NH, SO$_2$—NR9, CO—NH, CO—O, CO—S, 1,3-triazole, aminotriazine, triazinyl ether, NH—CO—NH, NH—CS—NH, NH—CO—O, O—POR9-O, SO$_2$—O, amino acid, aryl or heteroaryl,
wherein R9 is alkyl or WSG,
a and c can be the same or different and are an integer number 1 to 10, and
b is an integer number 0 to 10;
WSG is a water soluble group selected from sulfonic acid, sulfate, alkyl sulfonic acid, sulfonamide, phosphate, phosphonic acid, boronic acid, ammonium, pyridinium, monosaccharide and —(CH$_2$—CH$_2$—O)$_x$ in which x is an integer number from 1 to 10;
and salts thereof.

In one or more embodiments, in a 7-amino-3-thienyl coumarin dye of formula (II), (III) or (IV), Y may be selected from none, O, S, SO$_2$—NH, SO$_2$—NR9, CO—NH, CO—O, CO—S, 1,3-triazole, NH—CO—NH, NH—CS—NH, NH—CO—O, SO$_2$—O, aryl, heteroaryl and amino acid, preferably Y is selected from none, O, S, SO$_2$—NH, SO$_2$—NR9, CO—NH, CO—O and 1,3-triazole, wherein R9 is alkyl or WSG.

In one or more embodiments, in a 7-amino-3-thienyl coumarin dye of formula (II), (III) or (IV), WSG may be selected from sulfonic acid, alkyl sulfonic acid, sulfonamide, phosphate, phosphonic acid, ammonium, pyridinium, cyclodextrin, monosaccharide, oligosaccharide, dextrane and —(CH$_2$—CH$_2$—O)$_x$ in which x is an integer number from 1 to 10, preferably WSG is selected from sulfonic acid, alkyl sulfonic acid, sulfonamide, ammonium and —(CH$_2$—CH$_2$—O)$_x$ in which x is an integer number from 1 to 10.

In one or more embodiments, in a 7-amino-3-thienyl coumarin dye of formula (II), (III) or (IV), RG is selected from carboxylic acid, an activated ester of a carboxylic acid, sulfonyl halide, acyl halide, amine, alkyl or aryl halide, anhydride, azide, haloacetamide, halotriazine, hydrazine, isocyanate, isothiocyanate, maieimide, phosphoramidate, thiol, alcohol and alkyne, preferably RG is selected from carboxylic acid, an activated ester of a carboxylic acid, amine, azide, haloacetamide, hydrazine, isocyanate, maieimide and alkyne.

In one or more embodiments, a 7-amino-3-thienyl coumarin dye of formula (II), (III) or (IV) may be selected from:
sodium 5-(7-((5-carboxypentyl)(ethyl)amino)-2-oxo-2H-chromen-3-yl)thiophene-2,4-disulfonate;
sodium 5-(7-((6-((2,5-dioxopyrrolidin-1-yl)oxy)-6-oxohexyl)(ethyl)amino)-2-oxo-2H-chromen-3-yl)thiophene-2,4-disulfonate;
sodium 5-(7-(ethyl(6-hydrazinyl-6-oxohexyl)amino)-2-oxo-2H-chromen-3-yl)thiophene-2,4-disulfonate;
sodium 5-(7-((6-((2-(2,5-dioxo-2,5-dihydro-1H-pyrrol-1-yl)ethyl)amino)-6-oxohexyl)(ethyl)amino)-2-oxo-2H-chromen-3-yl)thiophene-2,4-disulfonate;
sodium 5-(7-((6-((2,5-dioxopyrrolidin-1-yl)oxy)-6-oxohexyl)(3-sulfonatopropyl)amino)-2-oxo-2H-chromen-3-yl)thiophene-2,4-disulfonate;
sodium 5-(9-(6-((2, 5-dioxopyrrolidin-1-yl)oxy)-6-oxohexyl)-2-oxo-6,7,8,9-tetrahydro-2H-pyrano[3,2-g]quinolin-3-yl)thiophene-2,4-disulfonate;
5-(7-((6-((2,5-dioxopyrrolidin-1-yl)oxy)-6-oxohexyl)(2-(2-methoxyethoxy)ethyl)amino)-2-oxo-2H-chromen-3-yl)thiophene-2,4-disulfonic acid;

5-(7-((6-((2,5-dioxopyrrolidin-1-yl)oxy)-6-oxohexyl)(2-oxo-2-((3-sulfopropyl)amino)ethyl)amino)-2-oxo-2H-chromen-3-yl)thiophene-2,4-disulfonic acid;

5-(7-((6-((2,5-dioxopyrrolidin-1-yl)oxy)-6-oxohexyl)(3-(N-(2-sulfoethyl)sulfamoyl)propyl)amino)-2-oxo-2H-chromen-3-yl)thiophene-2,4-disulfonic acid;

5-(7-((3-(N-(6-((2,5-dioxopyrrolidin-1-yl)oxy)-6-oxohexyl)sulfamoyl)propyl)(ethyl)amino)-2-oxo-2H-chromen-3-yl)thiophene-2,4-disulfonic acid;

5-(7-((4-(((2,5-dioxopyrrolidin-1-yl)oxy)carbonyl)benzyl)(ethyl)amino)-2-oxo-2H-chromen-3-yl)thiophene-2,4-disulfonic acid;

In one or more embodiments, a 7-amino-3-thienyl coumarin dye conjugate may have formula (V):

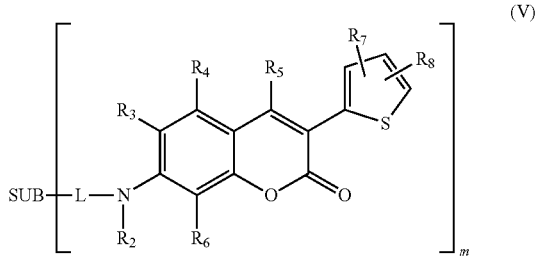

(V)

wherein

R2, R3, R4, R5, and R6 are independently selected from H, halogen, cyano, trifluoromethyl, WSG, L-WSG, substituted or unsubstituted alkyl and substituted or unsubstituted alkoxy;

R7 and R8 are sulfonic acid and are bound to the thienyl ring in positions 2 and 4, L is a linker of formula (VI):

(VI)

wherein Y is the same or different and is selected from none, O, S, NH, NR9, $SO_2$—NH, $SO_2$—NR9, CO—NH, CO—O, CO—S, 1,3-triazole, aminotriazine, triazinyl ether, NH—CO—NH, NH—CS—NH, NH—CO—O, O—POR9-O, $SO_2$—O, amino acid, aryl and heteroaryl, wherein R9 is alkyl or WSG, a and c can be the same or different and are an integer number 1 to 10, and b is an integer number 0 to 10;

WSG is a water soluble group and is selected from sulfonic acid, sulfate, alkyl sulfonic acid, sulfonamide, phosphate, phosphonic acid, boronic acid, ammonium, pyridinium, monosaccharide and —($CH_2$—$CH_2$—O)$_x$ in which x is an integer number from 1 to 10;

m is an integer number 1 to 25;

SUB is an amino acid, a peptide, a protein, a saccharide, a nucleoside, a nucleotide, an oligonucleotide, a nucleic acid, a hapten, a drug or a lipid;

and salts thereof.

In one or more embodiments, in a 7-amino-3-thienyl coumarin dye conjugate of formula (V), R3, R4, R5 and R6 may be hydrogen atoms.

In one or more embodiments, in a 7-amino-3-thienyl coumarin dye conjugate of formula (V), R2 is substituted or unsubstituted alkyl or L-WSG;

L is a linker of formula (VI):

(VI)

wherein Y is the same or different and is selected from none, O, S, NH, NR9, $SO_2$—NH, $SO_2$—NR9, CO—NH, CO—O, CO—S, 1,3-triazole, aminotriazine, triazinyl ether, NH—CO—NH, NH—CS—NH, NH—CO—O, O—POR9-O, $SO_2$—O, amino acid, aryl and heteroaryl, wherein R9 is alkyl or WSG, a and c can be the same or different and are an integer number 1 to 10, and b is an integer number 0 to 10;

WSG is a water soluble group and is selected from sulfonic acid, sulfate, alkyl sulfonic acid, sulfonamide, phosphate, phosphonic acid, boronic acid, ammonium, pyridinium, monosaccharide and —($CH_2$—$CH_2$—O)$_x$ in which x is an integer number from 1 to 10;

m is an integer number 1 to 25.

In one or more embodiments, a kit may comprise at least one 7 amino-3-thienyl coumarin of formula (II), (III) or (IV) as defined above.

In one or more embodiments, a kit may comprise at least one 7-amino-3-thienyl coumarin dye conjugate of formula (V) as defined above.

The invention claimed is:

1. A compound having formula (I):

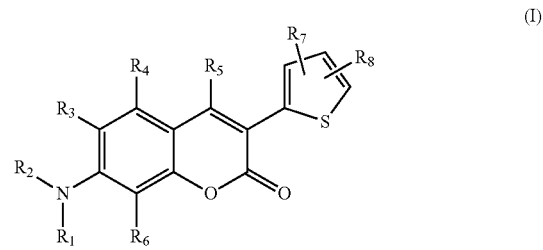

(I)

wherein $R_1$ is L-RG;

$R_2$, $R_3$, $R_4$, $R_5$, $R_6$, $R_7$ and $R_8$ are independently selected from H, halogen, alkenyl, alkynyl, cyano, trifluoromethyl, aryloxy, azido, amino, hydroxy, WSG, L-WSG, substituted or unsubstituted alkyl and substituted or unsubstituted alkoxy, wherein the substituted alkyl and substituted alkoxy are substituted with a substituent selected from the group consisting of: hydroxy, trifluoromethyl, halogen, alkoxy, aminoalkyl, aminoalkoxy, amino, monoalkylamino, dialkylamino, alkylcarbonylamino, alkoxycarbonylamino, alkoxycarbonyl, carboxy, hydroxyalkoxy, alkoxyalkoxy, monoalkylaminoalkoxy, (carboxyalkyl)amino, alkoxycarbonyl, alkynylcarbonyl, alkylsulfonyl, alkenylsulfonyl, alkynylsulfonyl, arylsulfonyl, alkylsulfonamido, arylsulfonamido, carboxyalkoxy, carboxyalkyl, carboxyalkylamino, cyano, trifluoromethoxy, guanidine, alkyl azide, azide, alkylthio, disulfide, acrylo, aryl, arylalkyl, heteroaryl, heteroarylalkyl, cycloalkylalkyl, cycloalkenylalkyl, cycloheteroalkylalkyl, cycloheteroalkenylalkyl and WSG;

$R_2$ together with $R_3$ may form a substituted or unsubstituted 6-membered N-heterocycle;

RG is a chemically reactive group selected from carboxylic acid, —COW or —(CO)W, wherein W is selected from succinimidyloxy, sulfosuccinimidyloxy, 1-oxbenzotriazolyl, a substituted or unsubstituted aryloxy group, wherein the one or more substituents are independently selected from nitro, fluoro, chloro, cyano, and trifluoromethyl, carbodiimide, sulfonyl halide, acyl halide, silyl halide, acyl azide, acyl nitrile, acrylamide, amine, formyl, alkyl halide, aryl halide, alkyl sulfonate, sulfonate ester, anhydride, azide, aziridine, diazoalkane, haloacetamide, halotriazine, hydrazine, hydroxylamine, isocyanate, isothiocyanate, maleimide, phosphoramidate, thiol, hydroxy, hydrazine and alkynyl;

L is a linker of formula (VI):

wherein

Y is independently selected from a bond, O, S, NH, NR$_9$, SO$_2$—NH, SO$_2$—NR$_9$, CO—NH, CO—O, C═N—NHR$_9$, CO—S, 1,2,3-triazolyl, CO—O—CO, aminotriazinyl, triazinyl ether, NH—CO—NH, NH—CS—NH, NH—CO—O, POR$_9$—O, SO$_2$, SO$_2$—O, amino acid, aryl or heteroaryl, wherein R$_9$ is alkyl or WSG, a and c are each independently 1, 2, 3, 4, 5, 6, 7, 8, 9 or 10, b is 0, 1, 2, 3, 4, 5, 6, 7, 8, 9 or 10; and WSG is a water soluble group selected from sulfonic acid, sulfate, alkyl sulfonic acid, thiosulfonic acid, sulfonamide, phosphate, phosphonic acid, boronic acid, ammonium, pyridinium, quinolium, acridinium, cyclodextrin, monosaccharide, oligosaccharide, dextrane and —(CH$_2$—CH$_2$—O)$_x$, in which x is 1, 2, 3, 4, 5, 6, 7, 8, 9 or 10;

with the proviso that at least one of R$_7$ and R$_8$ is WSG, and salts thereof.

2. The compound according to claim 1 having formula (II):

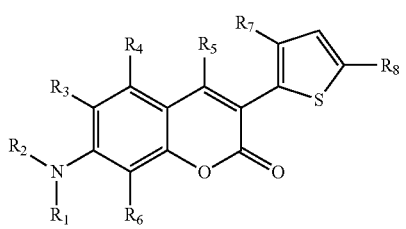

wherein

R$_2$, R$_3$, R$_4$, R$_5$, R$_6$, R$_7$ and R$_8$ are independently selected from H, halogen, cyano, trifluoromethyl, hydroxy, WSG, L-WSG, substituted or unsubstituted alkyl, and substituted or unsubstituted alkoxy;

with the proviso that at least one of R$_7$ and R$_8$ is a sulfonic acid;

and salts thereof.

3. The compound according to claim 1 having formula (III):

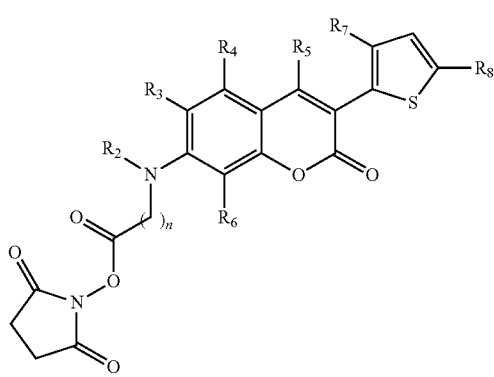

wherein

R$_2$ is selected from substituted or unsubstituted alkyl, and L-WSG;

R$_3$, R$_4$, R$_5$, R$_6$, R$_7$ and R$_8$ are independently selected from H, halogen, hydroxy, cyano, substituted or unsubstituted alkyl, and substituted or unsubstituted alkoxy;

and n is 1, 2, 3, 4, 5, 6, 7, 8, 9 or 10;

with the proviso that at least one of R$_7$ and R$_8$ is a sulfonic acid;

and salts thereof.

4. The compound according to claim 1 having formula (IV):

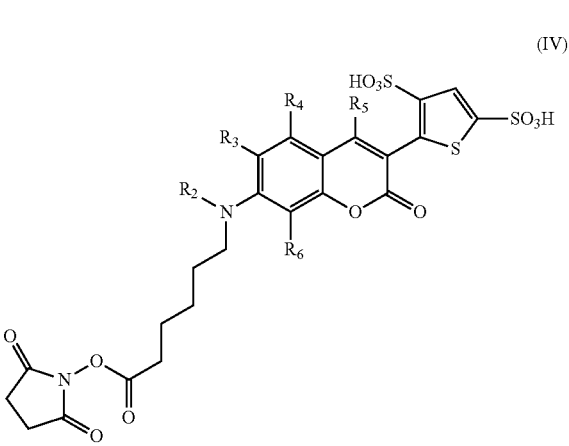

wherein

R$^2$ is selected from substituted or unsubstituted alkyl, and L-WSG;

and R$_3$, R$_4$, R$_5$, and R$_6$ are independently H;

and salts thereof.

5. The compound according to claim 1, wherein Y is selected from a bond, O, S, SO$_2$—NH, SO$_2$—NR$_9$, CO—NH, CO—O, CO—S, 1,2,3-triazolyl, NH—CO—NH, NH—CS—NH, NH—CO—O, SO$_2$—O, aryl, heteroaryl and amino acid.

6. The compound according to claim 5, wherein Y is selected from a bond, O, S, SO$_2$—NH, SO$_2$—NR$_9$, CO—NH, CO—O and 1,2,3-triazolyl.

7. The compound according to claim 1, wherein WSG is selected from sulfonic acid, alkyl sulfonic acid, sulfonamide, phosphate, phosphonic acid, ammonium, pyridinium, cyclodextrin, monosaccharide, oligosaccharide, dextrane and —(CH$_2$—CH$_2$—O)$_x$ in which x is 1, 2, 3, 4, 5, 6, 7, 8, 9 or 10.

8. The compound according to claim 7, wherein WSG is selected from sulfonic acid, alkyl sulfonic acid, sulfonamide, ammonium and —(CH$_2$—CH$_2$—O)$_x$ in which x is 1, 2, 3, 4, 5, 6, 7, 8, 9 or 10.

9. The compound according to claim 1, wherein RG is selected from carboxylic acid, —COW or —(CO)W, wherein W is selected from succiminidyloxy, sulfosuccinimidyloxy, 1-oxybezotriazolyl, a substituted or unsubstituted aryloxy group, wherein the one or more substituents are independently selected from nitro, fluoro, chloro, cyano, and trifluoromethyl, sulfonyl halide, acyl halide, amine, alkyl halide, aryl halide, anhydride, azide, haloacetamide, halotriazine, hydrazine, isocyanate, isothiocyanate, maleimide, phosphoramidate, thiol, hydroxy and alkynyl.

10. The compound according to claim 9, wherein RG is selected from carboxylic acid, —COW or —(CO)W, wherein W is selected from succiminidyloxy, sulfosuccinimidyloxy, 1-oxybenzotriazolyl, a substituted or unsubstituted aryloxy group, wherein the one or more substituents are independently selected from nitro, fluoro, chloro, cyano, and trifluoromethyl, amine, azide, haloacetamide, hydrazine, isocyanate, maleimide and alkynyl.

11. The compound according to claim 1, selected from:
sodium 5-(7-((5-carboxypentyl)(ethyl)amino)-2-oxo-2H-chromen-3-yl)thiophene-2,4-disulfonate;
sodium 5-(7-((6-((2,5-dioxopyrrolidin-1-yl)oxy)-6-oxohexyl)(ethyl)amino)-2-oxo-2H-chromen-3-yl)thiophene-2,4-disulfonate;
sodium 5-(7-(ethyl(6-hydrazinyl-6-oxohexyl)amino)-2-oxo-2H-chromen-3-yl)thiophene-2,4-disulfonate;
sodium 5-(7-((6-((2-(2,5-dioxo-2,5-dihydro-1H-pyrrol-1-yl)ethyl)amino)-6-oxohexyl)(ethyl)amino)-2-oxo-2H-chromen-3-yl)thiophene-2,4-disulfonate;
sodium 5-(7-((6-((2,5-dioxopyrrolidin-1-yl)oxy)-6-oxohexyl)(3-sulfonatopropyl)amino)-2-oxo-2H-chromen-3-yl)thiophene-2,4-disulfonate;
sodium 5-(9-(6-((2,5-dioxopyrrolidin-1-yl)oxy)-6-oxohexyl)-2-oxo-6,7,8,9-tetrahydro-2H-pyrano[3,2-g]quinolin-3-yl)thiophene-2,4-disulfonate;
5-(7-((6-((2,5-dioxopyrrolidin-1-yl)oxy)-6-oxohexyl)(2-(2-methoxyethoxy)ethyl)amino)-2-oxo-2H-chromen-3-yl)thiophene-2,4-disulfonic acid;
5-(7-((6-((2,5-dioxopyrrolidin-1-yl)oxy)-6-oxohexyl)(2-oxo-2-((3-sulfopropyl)amino)ethyl)amino)-2-oxo-2H-chromen-3-yl)thiophene-2,4-disulfonic acid;
5-(7-((6-((2,5-dioxopyrrolidin-1-yl)oxy)-6-oxohexyl)(3-(N-(2-sulfoethyl)sulfamoyl)propyl)amino)-2-oxo-2H-chromen-3-yl)thiophene-2,4-disulfonic acid;
5-(7-((3-(N-(6-((2,5-dioxopyrrolidin-1-yl)oxy)-6-oxohexyl)sulfamoyl)propyl)(ethyl)amino)-2-oxo-2H-chromen-3-yl)thiophene-2,4-disulfonic acid;
5-(7-((4-(((2,5-dioxopyrrolidin-1-yl)oxy)carbonyl) benzyl)(ethyl)amino)-2-oxo-2H-chromen-3-yl)thiophene-2,4-disulfonic acid;
2,2'-((5-(7-((6-((2,5-dioxopyrrolidin-1-yl)oxy)-6-oxohexyl)(ethyl)amino)-2-oxo-2H-chromen-3-yl)thiophene-2,4-disulfonyl)bis(azanediyl))bis(ethane-1-sulfonic acid); and
2,5-dioxopyrrolidin-1-yl 6-((3-(3,5-disulfamoylthiophen-2-yl)-2-oxo-2H-chromen-7-yl)(ethyl)amino)hexanoate.

12. A kit comprising at least one compound according to claim 1.

13. A compound having formula (V):

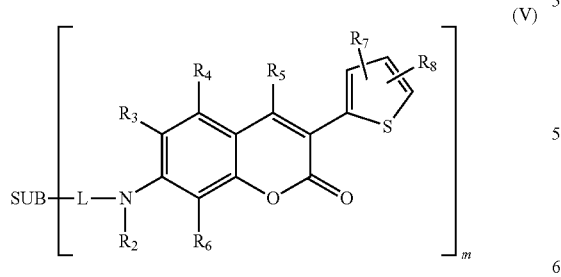

(V)

wherein
$R_2$, $R_3$, $R_4$, $R_5$, $R_6$, $R_7$ and $R_8$ are independently selected from H, halogen, alkenyl, alkynyl, cyano, trifluoromethyl, aryloxy, azido, amino, hydroxy, WSG, L-WSG, substituted or unsubstituted alkyl and substituted or unsubstituted alkoxy, wherein the substituted alkyl and substituted alkoxy are substituted with a substituent selected from the group consisting of: hydroxy, trifluoromethyl, halogen, alkoxy, aminoalkyl, aminoalkoxy, amino, monoalkylamino, dialkylamino, alkylcarbonylamino, alkoxycarbonylamino, alkoxycarbonyl, carboxy, hydroxyalkoxy, alkoxyalkoxy, monoalkylaminoalkoxy, (carboxyalkyl)amino, alkoxycarbonyl, alkynylcarbonyl, alkylsulfonyl, alkenylsulfonyl, alkynylsulfonyl, arylsulfonyl, alkylsulfonamido, arylsulfonamido, carboxyalkoxy, carboxyalkyl, carboxyalkylamino, cyano, trifluoromethoxy, guanidine, alkyl azide, azide, alkylthio, disulfide, acrylo, aryl, arylalkyl, heteroaryl, heteroarylalkyl, cycloalkylalkyl, cycloalkenylalkyl, cycloheteroalkylalkyl, cycloheteroalkenylalkyl and WSG;
$R_2$ together with $R_3$ may form a substituted or unsubstituted 6-membered N-heterocycle;
L is a linker of formula (VI):

$$[(CH_2)_3—Y—(CH_2)_b]_c \quad (VI)$$

wherein Y is independently selected from a bond, O, S, NH, $NR_9$, $SO_2$—NH, $SO_2$—$NR_9$, CO—NH, CO—O, C=N—$NHR_9$, CO—S, 1,2,3-triazolyl, CO—O—CO, aminotriazinyl, triazinyl ether, NH—CO—NH, NH—CS—NH, NH—CO—O, O—$POR_9$—O, $SO_2$, $SO_2$—O, amino acid, aryl and heteroaryl,
wherein $R_9$ is alkyl or WSG,
a and c are each independently 1, 2, 3, 4, 5, 6, 7, 8, 9 or 10,
b is 0, 1, 2, 3, 4, 5, 6, 7, 8, 9 or 10;
WSG is a water soluble group and is selected from sulfonic acid, sulfate, alkyl sulfonic acid, thiosulfonic acid, sulfonamide, phosphate, phosphonic acid, boronic acid, ammonium, pyridinium, quinolium, acridinium, cyclodextrin, monosaccharide, oligosaccharide, dextrane and —($CH_2$—$CH_2$—O)$_x$ in which x is 1, 2, 3, 4, 5, 6, 7, 8, 9 or 10;
m is 1, 2, 3, 4, 5, 6, 7, 8, 9, 10, 11, 12, 13, 14, 15, 16, 17, 18, 19, 20, 21, 22, 23, 24 or 25; and
SUB is an amino acid, a peptide, a protein, a saccharide, a nucleoside, a nucleotide, an oligonucleotide, a nucleic acid, a hapten, a drug or a lipid;
with the proviso that and at least one of $R_7$ and $R_8$ is a sulfonic acid,
and salts thereof.

14. The compound according to claim 13, wherein $R_2$ is substituted or unsubstituted alkyl or L-WSG.

15. The compound according to claim 13, wherein $R_3$, $R_4$, $R_5$ and $R_6$ are independently H.

16. The compound according to claim 13, wherein $R_7$ and $R_8$ are independently sulfonic acid and are bound to positions 2 and 4 of the thienyl ring.

17. A kit comprising at least one compound according to claim 13.

* * * * *

UNITED STATES PATENT AND TRADEMARK OFFICE
CERTIFICATE OF CORRECTION

PATENT NO. : 10,160,861 B2
APPLICATION NO. : 15/458801
DATED : December 25, 2018
INVENTOR(S) : Thomas Paul Jansen et al.

It is certified that error appears in the above-identified patent and that said Letters Patent is hereby corrected as shown below:

In the Claims

Column 50, Line 21, Claim 1, the word "fbrmula" should read "formula".

Column 50, Lines 61-62, Claim 1, the phrase "1-oxbenzotriazolyl" should read "1-oxybenzotriazolyl".

Column 51, Line 13, Claim 1, the phrase "POR9-O" should read "O-POR9-O".

Column 52, Line 59, Claim 9, the phrase "1-oxybezotriazolyl" should read "1-oxybenzotriazolyl".

Column 54, Line 25, Claim 13, the formula "[(CH2)3-Y-(CH2)b]c" should read "[(CH2)a-Y-(CH2)b]c".

Signed and Sealed this
Ninth Day of July, 2019

Andrei Iancu
*Director of the United States Patent and Trademark Office*